United States Patent [19]

Winternitz et al.

[11] Patent Number: 5,380,701
[45] Date of Patent: Jan. 10, 1995

[54] 3-ARYLURACIL DERIVATIVES AND THE USE THEREOF FOR WEED CONTROL

[75] Inventors: Paul Winternitz, Greifensee; Martin Zeller, Baden, both of Switzerland

[73] Assignee: Ciba-Geigy Corporation, Ardsley, N.Y.

[21] Appl. No.: 135,768

[22] Filed: Oct. 12, 1993

[30] Foreign Application Priority Data

Oct. 23, 1992 [CH] Switzerland ............... 3310/92

[51] Int. Cl.$^6$ ............... A01N 43/54; C07D 417/00; C07D 413/00; C07D 239/02
[52] U.S. Cl. ............... 504/243; 504/221; 504/225; 544/60; 544/123; 544/310; 544/311; 544/312; 544/313; 544/314
[58] Field of Search ............... 544/310–314, 544/60, 123; 504/243, 221, 225, 243

[56] References Cited

U.S. PATENT DOCUMENTS

| | | | |
|---|---|---|---|
| 4,746,352 | 5/1988 | Wenger | 544/311 |
| 4,812,164 | 3/1989 | Wenger et al. | 71/72 |
| 4,941,909 | 7/1990 | Wenger | 544/311 |
| 5,041,156 | 8/1991 | Suchy | 504/243 |
| 5,084,084 | 1/1992 | Satow et al. | 504/243 |
| 5,127,935 | 7/1992 | Satow et al. | 504/243 |
| 5,183,492 | 2/1993 | Suchy et al. | 504/243 |
| 5,232,898 | 8/1993 | Suchy et al. | 504/243 |

FOREIGN PATENT DOCUMENTS

| | | |
|---|---|---|
| 195346 | 9/1986 | European Pat. Off. . |
| 0260621 | 3/1988 | European Pat. Off. . |
| 8810254 | 12/1988 | WIPO . |
| 9015057 | 12/1990 | WIPO . |
| 9100278 | 1/1991 | WIPO . |

*Primary Examiner*—Cecilia Tsang
*Attorney, Agent, or Firm*—George R. Dohmann; Marla J. Mathias

[57] ABSTRACT

The invention relates to 3-aryluracils of formula I wherein
W is a group of formula $$-\overset{R_1}{\underset{|}{N}}-\overset{O}{\underset{\|}{C}}- \text{ or } -N=\overset{OR_{12}}{\underset{|}{C}}-,$$

in which the linkage to the ring nitrogen atom is through the carbon atom:

$R_1$ is hydrogen, $C_1$–$C_4$alkyl, $C_1$–$C_4$haloalkyl, $C_3$- or $C_4$alkenyl or $C_3$- or $C_4$alkynyl;
$R_2$ is halogen or cyano;
$R_3$ is hydrogen or fluoro;
$R_4$ is hydrogen, halogen or $C_1$–$C_4$alkyl;
$R_5$ is $C_1$–$C_4$alkyl or $C_1C_4$haloalkyl;
$R_6$ to $R_9$ are each independently of one another hydrogen, $C_1$–$C_4$alkyl, $C_3$–$C_6$alkenyl, $C_3$–$C_6$alkynyl, $C_1$–$C_4$haloalkyl or phenyl; or
$R_6$ and $R_7$ or $R_8$ and $R_9$, together with the linking carbon atom, form a 3-, 4-, 5- or 6-membered ring which may be substituted by one or more $C_1$–$C_4$alkyl groups; or $R_7$ and $R_9$, together with the linking carbon atoms, form a 3-, 4-, 5- or 6-membered ring which may be substituted by one or more $C_1$–$C_4$alkyl groups;
m is 0 or 1;
$R_{10}$ is hydrogen, $C_1C_4$alkyl, $C_3$- or $C_4$alkenyl, $C_3$- or $C_4$alkynyl, $C_1$–$C_4$haloalkyl, $C_1$–$C_6$alkoxy-$C_1$–$C_4$alkyl, $C_1$–$C_6$alkylthio-$C_1$–$C_4$alkyl;
$R_{11}$ is hydrogen, $C_1$–$C_4$alkyl, $C_3$- or $C_4$alkenyl, $C_3$–$C_5$alkynyl, $C_1$–$C_4$haloalkyl, $C_1$–$C_6$alkoxy, $C_1$–$C_6$alkenyloxy, $C_1$–$C_6$alkoxy-$C_1$–$C_4$alkyl, $C_1$–$C_6$alkylthio-$C_1$–$C_4$alkyl, $C_3$–$C_6$cycloalkyl, $C_2$–$C_4$cyanoalkyl, $C_1$–$C_4$alkoxycarbonyl-$C_1$- or -$C_2$alkyl, carboxy-$C_1$- or -$C_2$alkyl, $(C_1$–$C_4$alkoxy$)_2$-P(O)-$C_1$- or -$C_2$al- (Abstract continued on next page.)

Abstract—continued kyl, aryl, aryl-$C_1$-$C_4$alkyl, heteroaryl, heteroaryl-$C_1$-$C_4$alkyl, $C_3$-$C_6$cycloalkyl-$C_1$-$C_4$alkyl; or $R_{10}$ and $R_{11}$, together with the linking nitrogen atom, form a 4-, 5-, 6- or 7-membered ring which may be substituted by one or more $C_1$-$C_4$alkyl groups and which may contain —O—, —S— or —NH— as further hetero atoms; and $R_{12}$ is $C_1$-$C_4$alkyl, $C_3$- or $C_4$alkenyl or $C_3$- or $C_4$alkynyl; and, if $R_1$ is hydrogen, the agrochemically acceptable salts of the compounds of formula I.

The compounds are suitable for use as active ingredients of herbicidal compositions for weed control.

24 Claims, No Drawings

3-ARYLURACIL DERIVATIVES AND THE USE THEREOF FOR WEED CONTROL

The present invention relates to novel 3-aryluracil derivatives.

Herbicidal 3-aryluracils are known, inter alia, from WO 91/00278, which discloses in particular alkylsulfonylalkyl esters, alkoxycarbonylalkyl esters and cyanoalkyl esters.

A further class of 3-aryluracils having good herbicidal properties has now been found. Accordingly, the invention relates to 3-aryluracils of formula I

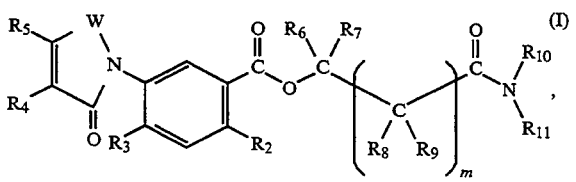

wherein
W is a group of formula

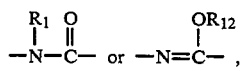

in which the linkage to the ring nitrogen atom is through the carbon atom:

$R_1$ is hydrogen, $C_1$–$C_4$alkyl, $C_1$–$C_4$haloalkyl, $C_3$- or $C_4$alkenyl or $C_3$- or $C_4$alkynyl;

$R_2$ is halogen or cyano;

$R_3$ is hydrogen or fluoro;

$R_4$ is hydrogen, halogen or $C_1$–$C_4$alkyl;

$R_5$ is $C_1$–$C_4$alkyl or $C_1$–$C_4$haloalkyl;

$R_6$ to $R_9$ are each independently of one another hydrogen, $C_1$–$C_4$alkyl, $C_3$–$C_6$alkenyl $C_3$–$C_6$alkynyl, $C_1$–$C_4$haloalkyl or phenyl; or $R_6$ and $R_7$ or $R_8$ and $R_9$, together with the linking carbon atom, form a 3-, 4-, 5- or 6-membered ring which may be substituted by one or more $C_1$–$C_4$alkyl groups; or $R_7$ and $R_9$, together with the linking carbon atoms, form a 3-, 4-, 5- or 6-membered ring which may be substituted by one or more $C_1$–$C_4$alkyl groups;

m is 0 or 1;

$R_{10}$ is hydrogen, $C_1$–$C_4$alkyl, $C_3$- or $C_4$alkenyl, $C_3$- or $C_4$alkynyl, $C_1$–$C_4$haloalkyl, $C_1$–$C_6$alkoxy-$C_1$–$C_4$alkyl, $C_1$–$C_6$alkylthio-$C_1$–$C_4$alkyl;

$R_{11}$ is hydrogen, $C_1$–$C_4$alkyl, $C_3$- or $C_4$alkenyl, $C_3$–$C_5$alkynyl, $C_1$–$C_4$haloalkyl, $C_1$–$C_6$alkoxy, $C_1$–$C_6$alkenyloxy, $C_1$–$C_6$alkoxy-$C_1$–$C_4$alkyl, $C_1$–$C_6$alkylthio-$C_1$–$C_4$alkyl, $C_3$–$C_6$cycloalkyl, $C_2$–$C_4$cyanoalkyl, $C_1$–$C_4$alkoxycarbonyl-$C_1$- or -$C_2$alkyl, carboxy-$C_1$- or -$C_2$alkyl, $(C_1$–$C_4$alkoxy$)_2$-P(O)-$C_1$- or -$C_2$alkyl, aryl, aryl-$C_1$–$C_4$alkyl, heteroaryl, heteroaryl-$C_1$–$C_4$alkyl, $C_3$–$C_6$cycloalkyl-$C_1$–$C_4$alkyl; or $R_{10}$ and $R_{11}$, together with the linking nitrogen atom, form a 4-, 5-, 6- or 7-membered ring which may be substituted by one or more $C_1$–$C_4$alkyl groups and which may contain —O—, —S— or —NH— as further hetero atoms; and $R_{12}$ is $C_1$–$C_4$alkyl, $C_3$- or $C_4$alkenyl or $C_3$- or $C_4$alkynyl; and, when $R_1$ is hydrogen, the agrochemically acceptable salts of the compounds of formula I.

Further objects of the invention are herbicidal compositions that contain the novel compounds, the preparation of these compounds, and the use of said compounds and compositions for controlling weeds.

In formula I of the novel 3-aryluracils, halogen in the definitions of the substituents $R_2$ and $R_4$ will be taken to mean fluoro, chloro, bromo and iodo. Fluoro, chloro and bromo are preferred. The alkyl, alkenyl and alkynyl substituents $R_1$ and $R_4$ to $R_{12}$ may be in straight-chain or branched-chain configuration, as may also apply to the alkyl moiety of haloalkyl, arylalkyl and alkoxy groups. Typical examples of such alkyl groups include methyl, ethyl, n-propyl, isopropyl, n-butyl, isobutyl, sec-butyl or tert-butyl. Typical examples of alkenyl groups are allyl, methallyl and but-2-en-1-yl; and exemplary alkynyl groups are propargyl, but-2-yn-1-yl, 2-methylbutyn-2-yl, but-3-yn-2-yl and pent-4-yn-1-yl. Alkoxyalkyl in the definitions of $R_{10}$ and $R_{11}$ may typically be methoxymethyl, methoxyethyl or ethoxyethyl. Alkoxy in the definition of $R_{11}$ may typically be methoxy, ethoxy, n-propoxy, isopropoxy, n-butoxy, isobutoxy and sec-butoxy. Alkylthio in the definitions of $R_{10}$ and $R_{11}$ is typically methylthio, ethylthio, n-propylthio, isopropylthio, n-butylthio, isobutylthio, sec-butylthio or tert-butylthio. A haloalkyl group may contain one or more than one (identical or different) halogen atom such as a fluorine, chlorine or bromine atom. Perhalogenated alkyl groups are typically trifluoromethyl and pentafluorethyl. The substituent of a cycloalkyl group $R_{11}$ may suitably be cyclopropyl, cyclobutyl, cyclopentyl or cyclohexyl. Aryl in the definition of $R_{11}$ is α- or β-naphthyl, preferably phenyl, wherein the aromatic rings may contain one or more than one identical or different substituent, typically halogen, preferably fluoro or chloro, C1–C3alkyl preferably methyl, C1–C3alkoxy, preferably methoxy, trifluoromethyl, nitro and/or cyano. Heteroaryl in the definition of $R_{11}$ is preferably a 5- or 6-membered aromatic heterocyclic ring such as 2-, 3- or 4-pyridyl, pyrimidyl, pyrazinyl, furanyl, thienyl, oxazolyl or isoxazolyl. Typical examples of 4- to 7-membered heterocyclic rings which $R_{10}$ und $R_{11}$ together may form are pyrrolidino, piperidino, hexahydroazepino, morpholino, 2,6-dimethylmorpholino, thiomorpholino, piperazino and 4-methylpiperazino.

Salts of compounds of formula I are preferably alkali metal salts, typically sodium and potassium salts; alkaline earth metal salts, typically calcium and magnesium salts; ammonium salts, i.e. unsubstituted ammonium salts and mono- or polysubstituted ammonium salts such as triethylammonium and methylammonium salts, as well as salts with other organic bases, conveniently with pyridine or quinuclidine.

The possible presence of at least one asymmetric carbon atom in the compounds of formula I means that the compounds can be obtained in the form of optically active individual isomers as well as in the form of racemic mixtures. In this invention, compounds of formula I will be understood as embracing both the pure optical antipodes as well as the racemates. Where no special reference is made to the individual optical antipodes, those racemic mixtures obtained in the described synthesis will be understood as falling under the indicated formula. If an aliphatic C=C double bond is present, then geometric isomerism can also occur. In addition, the occurrence of keto-enol tautomerism

is not ruled out in those compounds of formula I, wherein $R_1$ is hydrogen. Formula I will be understood as embracing all these possible isomers and mixtures thereof.

3-Aryluracil derivatives of formula I, wherein $R_2$ is chloro, bromo or cyano, are preferred.

Also preferred are those 3-aryluracil derivatives of formula I, wherein $R_4$ is hydrogen, fluoro or methyl.

3-Aryluracil derivatives of formula I, wherein $R_5$ is methyl, trifluoromethyl or pentafluoroethyl, are likewise preferred.

Other suitable 3-aryluracil derivatives of formula I are those wherein $R_6$ to $R_9$ are each independently of one another hydrogen, methyl, ethyl, $C_3$- or $C_4$alkenyl, $C_3$- or $C_4$alkynyl, $C_1$- or $C_2$haloalkyl or phenyl; or $R_6$ and $R_7$ or $R_8$ and $R_9$, together with the linking carbon atom form a 3-, 4-, 5- or 6-membered unsubstituted ring; or $R_7$ and $R_9$, together with the linking carbon atom form a 3-, 4-, 5- or 6-membered unsubstituted ring.

Further preferred 3-aryluracil derivates of formula I are those wherein $R_{10}$ is hydrogen, $C_1$-$C_4$alkyl, allyl, methallyl, propargyl or methoxy- or ethoxy-$C_2$-$C_4$alkyl.

Other preferred 3-aryluracil derivatives of formula I are those wherein $R_{11}$ is hydrogen, $C_1$-$C_4$alkyl, $C_3$alkenyl or $C_4$alkenyl, $C_3$-$C_5$ alkynyl, $C_1$-$C_4$alkoxy, $C_1$-$C_4$alkenyloxy, methoxy- or ethoxy-$C_2$-$C_4$alkyl, cyclopropyl, methoxy- or ethoxycarbonyl-$C_1$ - or -$C_2$alkyl, phenyl, benzyl, $C_6H_5CH(CH_3)$— or $C_3$-$C_6$cycloalkyl-$C_1$ - or -$C_2$alkyl, or wherein $R_{10}$ and $R_{11}$, together with the linking nitrogen atom, form a 5- or 6-membered ring which may be substituted by one or more than one methyl group and which may contain —O— or —S— as further hetero atom.

Particularly important 3-aryluracil derivatives of formula I are those wherein W and m are as defined for formula I; $R_2$ is chloro, bromo or cyano; $R_3$ is hydrogen or fluoro; $R_4$ is hydrogen, fluoro or methyl; $R_5$ is methyl, trifluoromethyl or pentafluoroethyl; $R_6$ to $R_9$ are each independently of one another hydrogen, methyl or ethyl; $R_{10}$ is hydrogen, $C_1$-$C_4$alkyl, allyl, methallyl or propargyl; $R_{11}$ is hydrogen, $C_1$-$C_4$alkyl, allyl, methallyl, $C_3$-$C_5$alkynyl, $C_1$alkoxy or $C_2$alkoxy, allyloxy, cyclopropyl, methoxy- or ethoxycarbonyl-$C_1$- or -$C_2$alkyl, phenyl, benzyl or $C_6H_5CH(CH_3)$—; or $R_{10}$ and $R_{11}$, together with the linking nitrogen atom, form a 5- or 6-membered unsubstituted ring which may contain —O— as further hetero atom.

Particularly suitable 3-aryluracil derivatives of formula I are those wherein W is a radical of formula

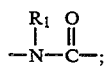

$R_1$ is hydrogen, $C_1$-$C_4$alkyl, $C_1$-$C_4$haloalkyl, $C_3$- or $C_4$alkenyl or $C_3$- or $C_4$alkynyl; $R_2$ is chloro; $R_3$ and $R_4$ are hydrogen; $R_5$ is trifluoromethyl; $R_6$ and $R_7$ are each independently of the other hydrogen or methyl; m is 0 or 1; $R_8$ and $R_9$ are hydrogen; $R_{10}$ is hydrogen or $C_1$-$C_4$alkyl; $R_{11}$ is hydrogen, $C_1$-$C_4$alkyl, allyl, $C_3$-$C_5$alkynyl, $C_1$alkoxy or $C_2$alkoxy, allyloxy, cyclopropyl, ethoxycarbonyl-$C_1$- or -$C_2$alkyl, phenyl, benzyl or $C_6H_5CH(CH_3)$—; or $R_{10}$ and $R_{11}$, together with the linking nitrogen atom, form a 5- or 6-membered unsubstituted ring which may contain —O— as further hetero atom. Among these compounds of formula I, the compounds of special preference are those wherein $R_1$ is hydrogen, allyl or propargyl, preferably methyl.

Also particularly suitable are the 3-aryluracil derivatives of formula I, wherein W is a radical of formula

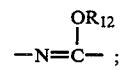

$R_{12}$ is $C_1$-$C_4$alkyl, $C_3$- or $C_4$alkenyl or $C_3$- or $C_4$alkynyl; $R_2$ is chloro, bromo or cyano; $R_3$ is hydrogen or fluoro; $R_4$ is hydrogen, fluoro, chloro or methyl; $R_5$ is methyl, trifluoromethyl or pentafluoroethyl; $R_6$ and $R_7$ are each independently of the other hydrogen or methyl; m is 0 or 1; $R_8$ and $R_9$ are hydrogen; $R_{10}$ is hydrogen or methyl; and $R_{11}$ is hydrogen, $C_1$-$C_4$alkyl or allyl.

Other 3-aryluracil derivatives of formula I which merit special importance are those compounds wherein m is 1; $R_6$ is methyl; and $R_7$ is hydrogen.

3-Aryluracil derivatives of very special importance are those compounds of formula Ia

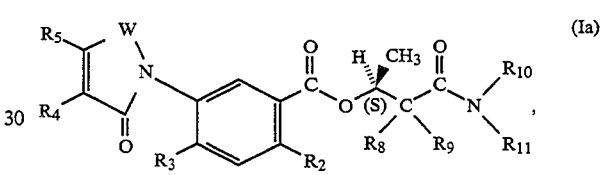

wherein W, $R_1$ to $R_5$ and $R_8$ to $R_{12}$ are as defined for formula I

3-Aryluracil derivatives of prime importance are the compounds of formula Ib

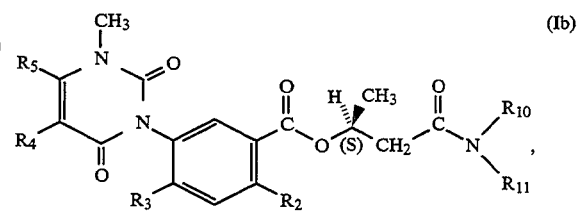

wherein $R_2$ is chloro, bromo or cyano; $R_3$ is hydrogen or fluoro; $R_4$ is hydrogen, methyl or fluoro; $R_5$ is methyl, trifluoromethyl or pentafluoroethyl; $R_{10}$ and $R_{11}$ are each independently of the other hydrogen or $C_1$-$C_4$alkyl.

Compounds of the first importance are those of formula Ic

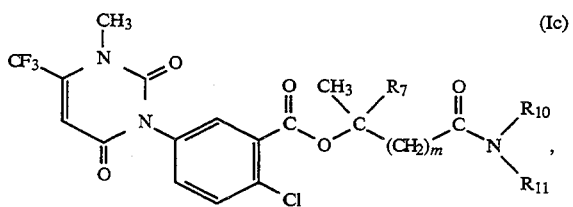

wherein $R_7$ is hydrogen or methyl; m is 0 or 1; $R_{10}$ is hydrogen or $C_1$-$C_4$alkyl; $R_{11}$ is hydrogen, $C_1$-$C_4$alkyl, allyl, $C_3$-$C_5$alkynyl, cyclopropyl, ethoxycarbonyl-$C_1$- or -$C_2$alkyl, phenyl, benzyl or $C_6H_5CH(CH_3)$—; or $R_{10}$ and $R_{11}$, together with the linking nitrogen atom, form a 5- or 6-membered unsubstituted ring which may contain —O— as further hetero atom.

Preferred individual compounds are those of formula Id

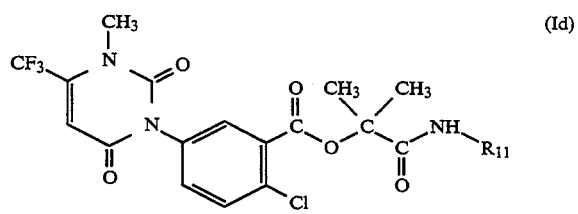
(Id)

wherein $R_{11}$ is $C_1$-$C_4$alkyl, allyl, propargyl, $C_1$- or $C_2$alkoxy or allyloxy.

The process of this invention for the preparation of the compounds of formula I and the salts thereof is carried out in general accordance with known procedures and comprises a) to prepare those 3-aryluracil derivatives of formula I, wherein $R_1$ is hydrogen, and metal salts of these compounds, cyclising a compound of formula IIa or IIb

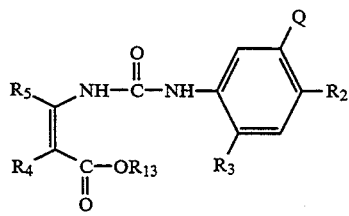
(IIa)

or

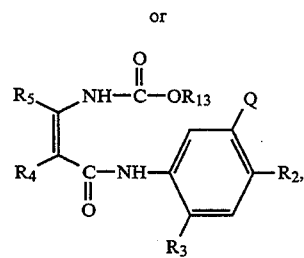
(IIb)

wherein $R_2$ to $R_5$ are as defined for formula I, $R_{13}$ is $C_1$-$C_6$alkyl, preferably methyl or ethyl, or $C_1$-$C_4$haloalkyl, preferably $C_1$- or $C_2$haloalkyl, Q is a group of formula

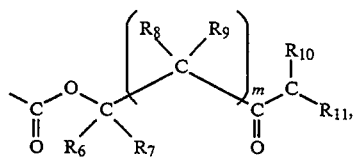

wherein $R_6$ to $R_{11}$ and m are as defined for formula I, in the presence of a base, and converting the salt of formula IIc

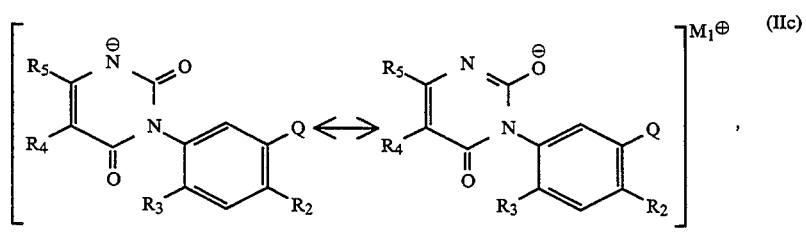
(IIc)

wherein $R_2$ to $R_5$ and Q have the given meanings and $M_1^\oplus$ is a cation, conveniently an alkali metal ion, by treatment with an acid into the compound of formula I, wherein $R_1$ is hydrogen;

b) to prepare those 3-aryluracil derivatives of formula I, wherein $R_1$ in the group W is $C_1$-$C_4$alkyl, $C_3$alkenyl or $C_4$alkenyl, $C_3$alkynyl or $C_4$alkynyl or $C_1$-$C_4$haloalkyl, alkylating a uracil derivative of formula Ig

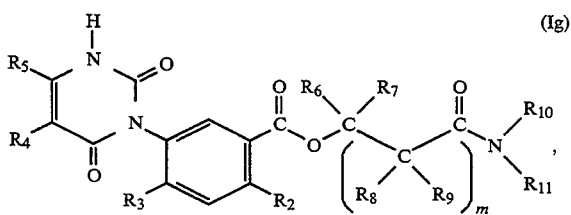
(Ig)

wherein $R_2$ to $R_{11}$ and m are as defined for formula I, in the presence of an alkylating agent containing a suitable $C_1$-$C_4$alkyl, $C_3$alkenyl or $C_4$alkenyl, $C_3$alkynyl or $C_4$alkynyl or $C_1$-$C_4$haloalkyl group; as further product it is also possible to obtain the O-alkylation product of formula If

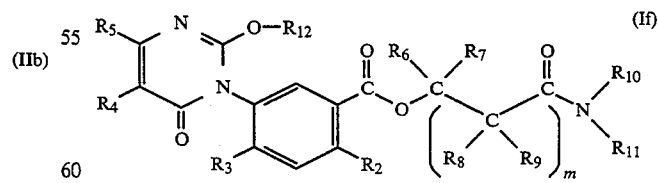
(If)

wherein $R_2$ to $R_{12}$ and m are as defined for formula I;

c) to prepare those 3-aryluracil derivatives of formula I in which $R_1$ in the group W is $C_1$-$C_4$alkyl, $C_1$-$1C_4$haloalkyl, $C_3$alkenyl or $C_4$alkenyl or $C_3$alkynyl or $C_4$alkynyl, esterifying a carboxylic acid derivative of formula III

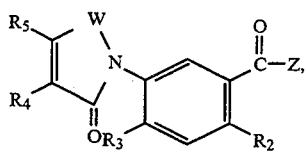

(III)

wherein Z is hydroxyl, halogen, preferably chloro, or a leaving group, preferably acetate, formate, benzoate, imidazolide, triazolide or N-hydroxyphthalimide; the group W and $R_2$ to $R_5$ are as defined for formula I, and $R_1$ in the group W has the given meaning, with a compound of formula IV

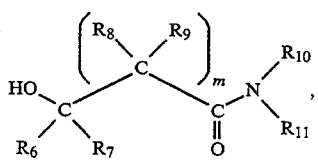

(IV)

wherein $R_6$ to $R_{11}$ and m are as defined for formula I, under customary conditions;

d) to prepare those 3-aryluracil derivatives of formula I in which $R_1$ in the group W is $C_1$–$C_4$alkyl, $C_1$–$C_4$ haloalkyl, $C_3$alkenyl or $C_4$alkenyl or $C_3$alkynyl or $C_4$alkynyl, esterifying a carboxylic acid derivative of formula III

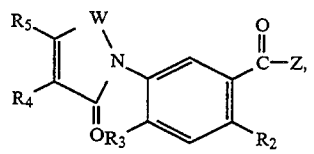

(III)

wherein the group W, Z and $R_2$ to $R_5$ have the given meanings, with a compound of formula V

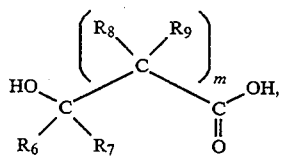

(V)

wherein $R_6$ to $R_9$ and m are as defined for formula I, to a compound of formula VI

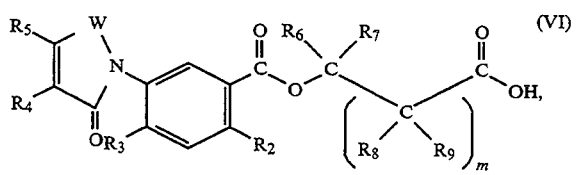

(VI)

under customary conditions. The carboxylic acid of formula VI is subsequently convened into a carboxlic acid derivative of formula VIa

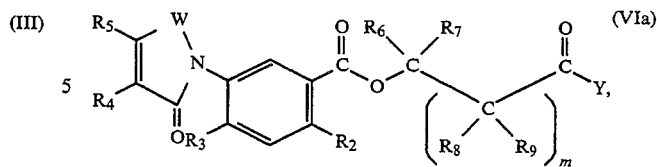

(VIa)

wherein the group W, $R_2$ to $R_9$ and m have the given meanings and Y is a leaving group, preferably halogen, more particularly chloro, and thereafter reacting said derivative with an amine of formula VII

(VII)

wherein $R_{10}$ and $R_{11}$ are as defined for formula I.

The cyclisation of process variants a) and b) is carried out in general accordance with U.S. Pat. No. 4,746,352.

The reaction of process variant c) is carried out by the methods described in S. Patai, "The Chemistry of Carboxylic Acids and Esters", Interscience Publishers, London, 1969; Houben-Weyl, Vol. VIII, page 508 ff.; Synthesis 1981, 333; J. Med. Chem. 17, 337 (1974); Synth. Communic. 1984, 353; and Chemistry Lett. 1985, 123.

The esterification of a 3-aryluracil derivative of formula III, wherein Z has the given meaning, with an alcohol of formula V in process variant d) is conveniently carried out in general accordance with process variant c). The subsequent amidation of the reactive carboxylic acid derivative of formula VIa is carried out in accordance with the methods described in Houben-Weyl, Vol. VIII, page 653 ff. and Vol. XI/2, page 3 ff.; J. Zabicky, "The Chemistry of Amides", Interscience Publishers, New York, 1970, Tetrahedron Lett. 1970, 1901; J. Org. Chem. 26, 2554 (1964); Chemistry Lett. 1985, 123; Synthesis 1983, 908; and Bull. Chem. Soc. Japan 57,85 (1984).

The salts of the compounds of formula I so obtained in which $R_1$ is hydrogen can be prepared in per se known manner, conveniently by dissolving a salt of the compounds of formula I in a solution of a suitable inorganic or organic base. Salt formation is usually effected within a short time at room temperature. In one embodiment of the process, the sodium salt is prepared by dissolving the uracil derivative of formula I in an aqueous solution of sodium hydroxide at room temperature using equivalents of the uracil derivative and sodium hydroxide. The solid salt can then be isolated by precipitation with a suitable inert solvent or by evaporation of the solvent. A further embodiment of the process consists in introducing an aqueous solution of an alkali metal salt of the uracil of formula I into an aqueous solution of a salt that contains a metal cation other than an alkali metal cation to give the second metal salt of the uracil derivative. This embodiment of the process normally serves to prepare uracil metal salts that are insoluble in water.

The compounds of formula I and their salts can be isolated and purified by per se known methods. Those skilled in the art will be familiar with the order in which certain reactions in accordance with process variants a)

to d) shall conveniently be carried out in order to avoid possible undesirable competing reactions.

Provided no planned synthesis to isolate pure isomers is carried out, the product can be obtained as a mixture of two or more isomers. The isomers can be separated by per se known methods. If desired, pure optically active isomers may also be synthesised from appropriate optically active starting materials.

The starting compounds of formulae IIa and IIb can be prepared in general accordance with known procedures, inter alia as described in EP-A-0 260 621, conveniently in accordance with the following reaction schemes 1 and 2 [methods aa), bb), cc), dd), ee) und ff)].

Reaction scheme method aa):

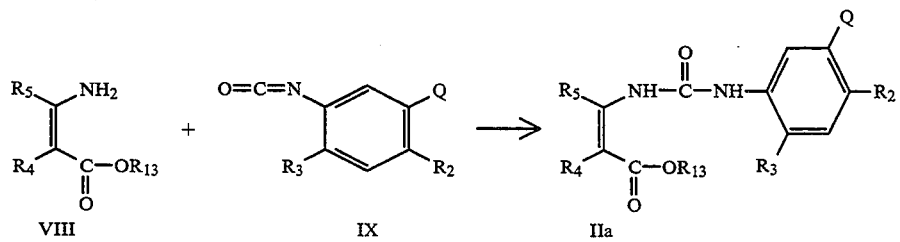

method bb):

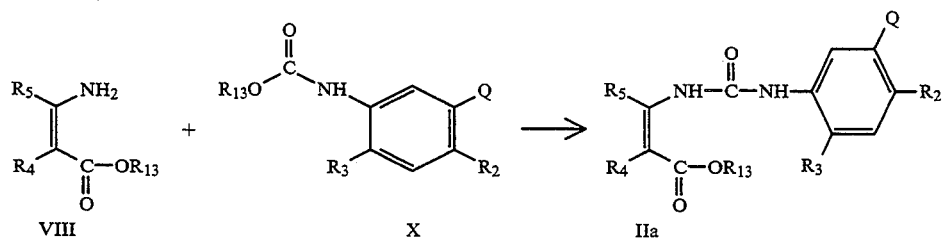

method cc):

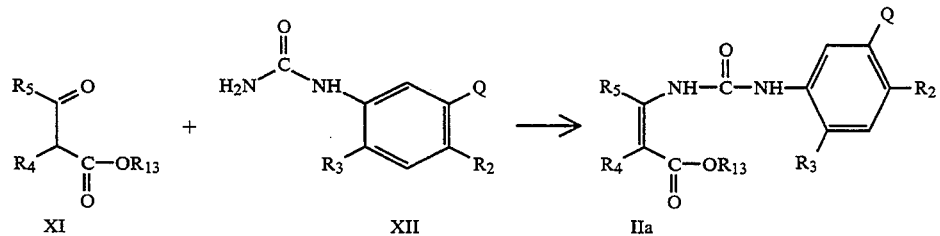

method dd)

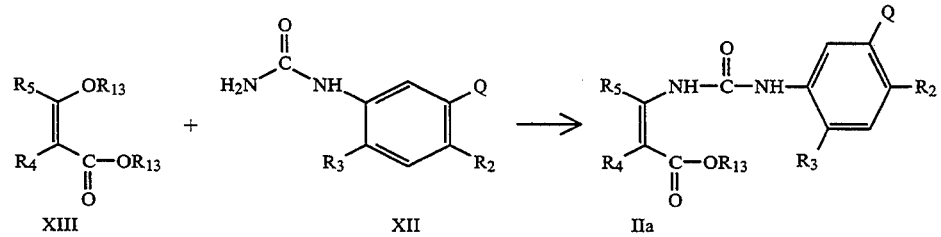

Reaction Scheme 2 method ee):

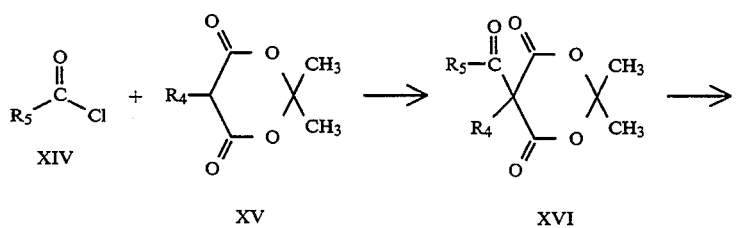

-continued
Reaction Scheme 2

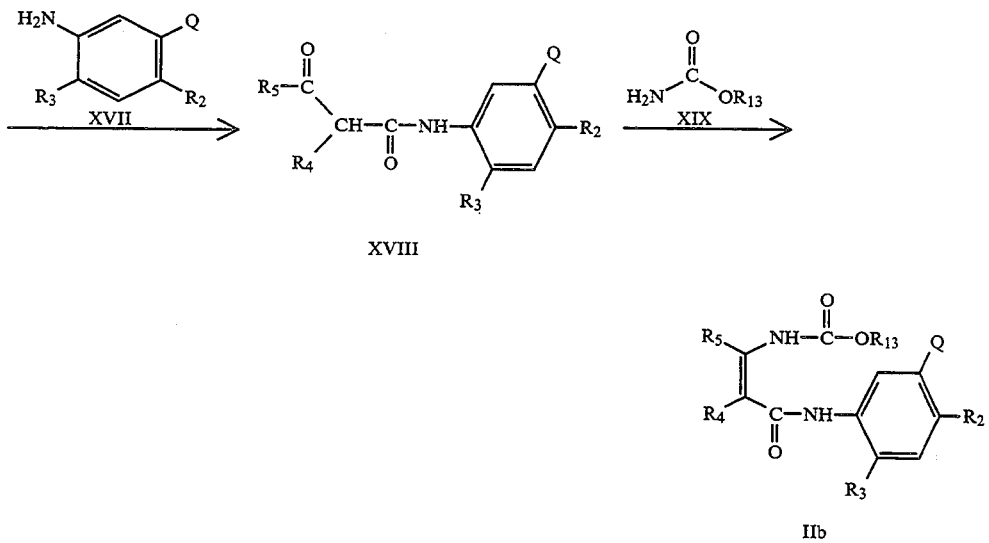

method ff):

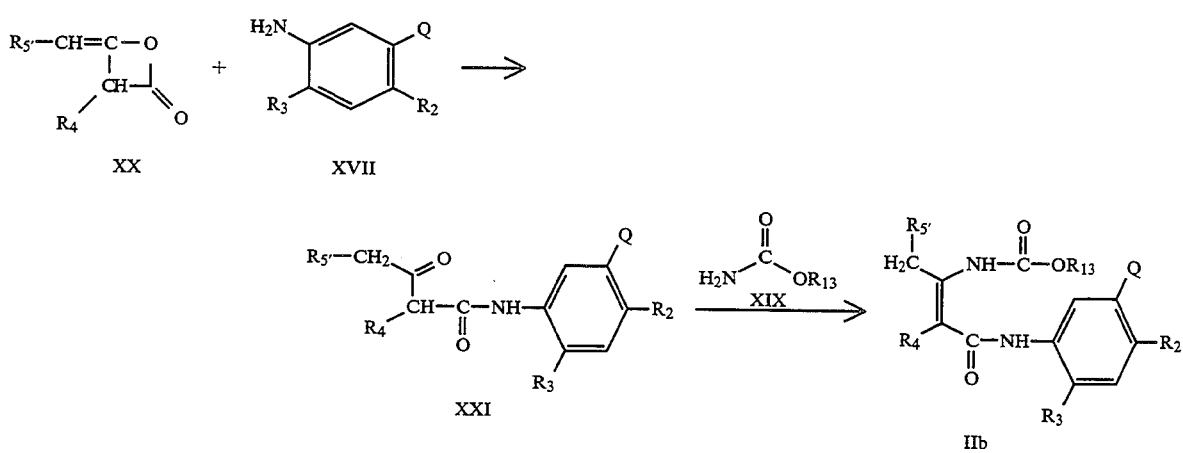

The reaction according to methods aa) to dd) in reaction scheme 1 is carried out in general accordance with EP-A-0 260 621.

The reaction according to methods ee) and ff) in reaction scheme 2 is carried out in general accordance with WO 90/15057.

The requisite starting compounds VIII, XI, XIII, XIV, XV, XIX und XX in process variants aa) to ff are known.

The starting compound of formula IX (variant aa)) can be prepared by known analogous methods from the compound of formula XVII by phosgenation or diphosgenation.

The starting compound of formula X (variant bb)) can be prepared by known analogous methods from the compound of formula XVII by reaction with chloroformates.

The starting compound of formula XII (variant cc)) can be prepared by known analogous methods from the compound of formula XVII by reaction with metal cyanates.

The starting compound of formula XVII (variants ee and ff))) can be prepared by known analogous methods from the compound of formula XXII

by reduction of the nitro group.

The starting compound of formula XXII can be prepared by known analogous methods from the compound of formula XXIII

[Structure: benzene ring with Q, $R_3$, $R_2$ substituents] (XXIII)

by nitration.

The intermediates of formulae VI and VIa are novel and have been specially synthesised for the synthesis of the novel compounds of formula I and constitute a further object of the invention.

It has now been found that the novel compounds of formula I (also referred to hereinafter as "herbicides"), as well as their enol ethers or salts, are useful compounds having herbicidal properties and are suitable for the selective postemergence and, preferably, preemergence control of weeds, including grass weeds, inter alia *Abutilon theophrasti, Amaranthus retroflexus, Cassia obtusifolia, Chenopodium album, Chrysanthemum segetum, Datura stramonium, Digitaria sanguinalis, Echinochloa crus-galli, Galium aparine, Matricaria chamomilla, Sinapis arvensis, Setaria faberii* and *Xanthium pennsylvanicum*, in different crops of useful plants, typically vines, fruit, oil palm and rubber plantations, as well as for application to industrial sites and in no-till farming. In addition, the compounds are suitable for use as weed deflagrators for facilitating the harvesting of potatoes and cotton.

In practice a concentration of 1 g to 2 kg/ha of compound of formula I, preferably of 10 g to 1 kg/ha, will normally suffice to achieve the desired herbicidal effect. The concentration range from 15 to 500 g/ha is especially useful for achieving the desired herbicidal effect combined with optimum tolerance towards the crop plants.

The novel herbicides contain an effective amount of at least one compound of formula I or of an enol ether or salt thereof, usually together with formulation assistants. They conveniently contain at least one formulation assistant selected from each of the following groups:
solid carriers,
solvents and/or dispersants
surfactants (wetting agents and emulsifiers),
dispersants (nonsurfactants) and
stabilisers.

The pesticidal formulations usually comprise, in addition to the herbicides of formula I, 5 to 99.9% of a formulation assistant selected from the group consisting of
solid carriers,
solvents and/or dispersants
dispersants (nonsurfactants) and
stabilisers; and to 25%, preferably 0.1 to 25%, of a surfactant (wetting agents and emulsifiers).

Using these and other adjuvants, the compounds of formula I, i.e. the herbicides, can be processed to the customary formulations such as dusts, powders, granulates, solutions, emulsions, suspensions, emulsifiable concentrates, pastes and the like.

The compounds of formula I and their enol ethers are normally water-insoluble, whereas the salts, especially the alkali metal salts and ammonium salts, are ordinarily water-soluble and can be formulated by the conventional methods used for water-insoluble and water-soluble compounds using known formulation assistants. The preparation of the compositions can be effected in a manner known per se, conveniently by mixing the appropriate herbicide with solid carriers, by suspending the herbicide in suitable solvents or dispersants with or without the addition of surfactants as wetting agents or emulsifiers and/or of dispersants, or by diluting already prepared emulsifiable concentrates with solvents or dispersants.

Typical examples of suitable solid carriers are:
natural mineral substances such as chalk, dolomite, limestone, clays and silica or salts thereof, including diatomaceous earth, kaolin, bentonite, tacum, attapulgite or montmorillonite;
synthetic mineral substances such as highly dispersed silica, alumina or silicates;
organic materials such as cellulose, starch, ureas or synthetic resins; or
fertilisers such as phosphates or nitrates.

Such carriers may be in powder or granular form.

Suitable solvents or dispersants essentially comprise: aromatic compounds such as benzene, toluene, xylenes and alkylnaphthalenes; chlorinated aromatic compounds mid chlorinated aliphatic hydrocarbons, including chlorobenzenes, chloroethylenes or methylene chloride; aliphatic hydrocarbons such as cyclohexane or paraffins, typically mineral oil fractions; alcohols such as butanol or glycol and the ethers and esters thereof; ketones such as acetone, methyl ethyl ketone, methyl isobutyl ketone or cyclohexanone; or strongly polar solvents or dispersants such as dimethyl formamide; N-methylpyrrolidone or dimethyl sulfoxide (which solvents preferably have flash points of at least 30° C. and boiling points of at least 50° C.) or water. Further suitable solvents and diluents are liquified gaseous extenders or carriers that are products which are gaseous at room temperature and under normal pressure. Illustrative examples of such products are especially aerosol propellant gases such as halogenated hydrocarbons, typically dichlorodifluoromethane. If the herbicide is in the form of a pressurised gas pack, then it is useful to add a solvent to the propellant gas.

The surfactants (wetting agents and emulsifiers) may be nonionic compounds such as condensates of fatty acids, fatty alcohols or fatty-substituted phenols with ethylene oxide; fatty acid esters and ethers of sugars or polyhydric alcohols; the products that are obtained from sugars or polyhydric alcohols by condensation with ethylene oxide; block polymers of ethylene oxide and propylene oxide; or alkyldimethylamine oxides.

The surfactants may also be anionic compounds including soaps; fatty sulfate esters, typically sodium dodecyl sulfate, sodium octadecyl sulfate and sodium cetyl sulfate; alkylsulfonates, arylsulfonates or fatty aromatic sulfonates such as alkylbenzenesulfonates, typically calcium dodecyl benzenesulfonate, or butylnaphthalenesulfonates; or more complex fatty sulfonates such as the amide condensates of oleic acid and N-methyltaurine or the sodium dioctylsulfosuccinate.

Finally, the surfactants may be cationic compounds such as alkyldimethylbenzylammonium chlorides, dialkyldimethylammonium chlorides, alkyltrimethylammonium chlorides or ethoxylated ammonium chlorides.

Suitable dispersants (nonsurfactants) may essentially be lignin, sodium and ammonium salts of ligninsulfonic acids, sodium salts of maleic anhydride-diisobutylene copolymers, sodium and ammonium salts of sulfonated polycondensates of naphthalene and formaldehyde, or sulfite lyes.

Dispersants that may suitably be used as thickeners or antiprecipitants are methyl cellulose, carboxymethyl cellulose, hydroxyethyl cellulose, polyvinyl alcohol, alginates, caseinates and blood albumin.

Typical examples of suitable stabilisers are: acid acceptors such as epichlorohydrin, phenyl glycidyl ethers or epoxidised soybean oil; antioxidants such as gallates or butyl hydroxytoluene; UV absorbers such as substituted benzophenones, diphenylacrylonitrilates or cinnamates; or deactivators, conveniently salts of ethylenediaminetetracetic acid and polyglycols.

The novel herbicides usually contain from 0.1 to 95% by weight, preferably from 0.5 to 75% by weight, of one or more than one novel compound of formula I as herbicide. They may be processed to formulations suitable for storage and transportation. The concentration of herbicide in such formulations, typically emulsifiable concentrates, is normally in a high range, preferably from 1 to 50% by weight, most preferably from 5 to 30% by weight. These formulations can then be diluted with identical or different inert substances to a concentration suitable for use in practice, i.e. preferably to c. 0.1 to 10% by weight, most preferably c. 0.5 to 5% by weight. The concentration of herbicide may, however, also be lower or higher.

As mentioned, the novel herbicidal compositions can be prepared in a manner known per se.

To prepare powder formulations, the herbicide, i.e. at least one compound of formula I, can be mixed with a solid carrier, conveniently by milling. Alternatively, the solid carrier can be impregnated with a solution or suspension of the herbicide and the solvent subsequently removed by evaporation, heating or exhaustion under reduced pressure. By addition of surfactants or dispersants such powder formulations can be made readily wettable with water so that they can be converted into aqueous suspensions that are suitable for use as spray mixtures.

The herbicide of formula I can also be mixed with a surfactant and a solid carrier to form a water-dispersible wettable powder, or it can be mixed with a solid pre-granulated carrier to form a granular product.

If desired, the herbicide of formula I can be dissolved in a water-immiscible solvent, conveniently a high boiling hydrocarbon. This solvent advantageously contains an emulsifier dissolved therein, so that the solution is self-emulsifying when added to water. Alternatively, the herbicide can be mixed with an emulsifier and the mixture then diluted with water to the desired concentration. In addition, the herbicide can be dissolved in a solvent and afterwards mixed with an emulsifier. Such a mixture can likewise be diluted with water to the desired concentration. It is thus possible to obtain emulsifiable concentrates or ready-for-use emulsions.

The novel use of the above described herbicidal formulations can be carried out by standard methods of application such as spraying, dusting, drenching or scattering.

The following Examples illustrate the invention in more detail.

A. PREPARATION OF THE NOVEL COMPOUNDS OF FORMULA I

Example P1

2-(Morpholinocarbamoyl)-1-methylethyl-2-chloro-5-[3,6-dihydro-3-methyl-2,6-dioxo-4-trifluoromethyl-1(2H)-pyrimidinyl]benzoate (compound 1.001)

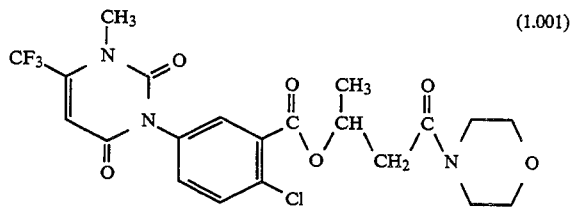

(1.001)

8.7 g of β-butyrolactone is charged to a reactor at 0° C. and 8.61 g of morpholine are added dropwise over 15 minutes, the temperature rising to 15° C. The cooling bath is removed and the temperature rises rapidly to 100° C. If desired, the temperature is kept at 100° C. with the cooling bath. The reaction mixture is stirred until the reaction is complete, i.e. until the reaction mixture has cooled to 20° C. The intermediate so obtained, 4-(3'-hydroxy-1'-oxobutyl)morpholine, is used in the subsequent reaction step without further purification.

0.15 g of pyridine is added dropwise to a mixture of 2.0 g of 2-chloro-5-[3,6-dihydro-2, 6-dioxo-3-methyl-4-trifluoromethyl-1-(2H)-pyrimidinyl]benzoyl chloride and 1.13 g of 4-(3'-hydroxy-1'-oxobutyl)morpholine in 25 ml of methylene chloride at room temperature and the reaction mixture is stirred for 1 hour. The reaction mixture is concentrated and the residue is taken up in 10 ml of ethyl acetate. The solution is washed with 10 ml each of 2N hydrochloric acid and water, dried over sodium sulfate and concentrated. The residue is chromatographed on 50 g of silica gel with ethyl acetate/n-hexane 3/1 as eluant. The product, 2-(morpholinocarbamoyl)-1-methylethyl-2-chloro-5-[3,6-dihydro-3-methyl-2,6-dioxo-4-trifluoromethyl-1(2H)-pyrimidinyl]benzoate is isolated as a colourless oil; $^1$H-NMR (CDCl$_3$, 200 MHz): 7.70 ppm (d, 1H), 7.60 ppm (d, 1H), 7.42 ppm (dxd, 1H), 6.38 ppm (s, 1H), 5.52 ppm (m, 1H), 3.59 ppm (s and m, 11H), 2.70 ppm (m, 2H), 1.48 ppm (d, 6H).

The compounds of formula Ih listed in the following Table 1 are prepared in accordance with the general procedure for obtaining compound 1.00 1.

TABLE 1

Compounds of formula Ih

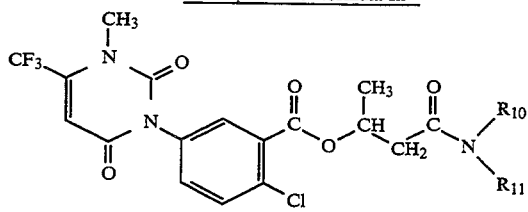

(Ih)

| Cmpd. | R$_{10}$ | R$_{11}$ | Physico-chemical data |
|---|---|---|---|
| 1.002 | —CH$_3$ | n-C$_4$H$_9$ | $^1$H-NMR (200 MHz, CDCl$_3$): 7.70 ppm (d, 1H), 7.58 ppm (dxd, 1H), 7.26 ppm (dxd, 1H), 6.38 ppm (s, 1H), 5.56 ppm (m, 1H), 3.55 ppm (s, 3H), 3.32 ppm (m, 2H), 2.88 and 3.00 ppm (2s, 3H), 2.72 ppm (m, 2H), 1.20– |

TABLE 1-continued

Compounds of formula Ih (Ih)

| Cmpd. | R₁₀ | R₁₁ | Physico-chemical data |
|---|---|---|---|
| | | | 1.64 ppm (m and d, 7H), 0.92 ppm (2t, 3H). |
| 1.003 | n-C₄H₉ | n-C₄H₉ | ¹H-NMR (200 MHz, CDCl₃): 7.70 ppm (dxd, 1H), 7.58 ppm (dxd, 2H), 7.28 ppm (dxd, 1H), 6.38 ppm (s, 1H), 5.58 ppm (m, 1H), 3.56 ppm (s, 3H), 3.30 ppm (m, 4H), 2.72 ppm (m, 2H), 1.18–1.62 ppm (m and d, 11H), 0.92 ppm (2t, 6H). |
| 1.004 | —CH₃ | phenyl | ¹H-NMR (200 MHz, CDCl₃): 7.14–7.70 ppm (m, 8H), 6.38 ppm (s, 1H), 5.56 ppm (m, 1H), 3.55 ppm (s, 3H), 3.25 ppm (s, 3H), 2.48 ppm (m, 2H), 1.35 ppm (d, 3H). |
| 1.005 | —CH₃ | benzyl (—CH₂—C₆H₅ via ethyl) | ¹H-NMR (200 MHz, CDCl₃): 7.12–7.70 ppm (m, 8H), 6.38 ppm (s, 1H), 5.62 ppm (m, 1H), 4.44–4.72 ppm (m, 2H), 3.54 ppm (s, 3H), ..90–3.05 ppm (m and s, 4H), 2.60 ppm (m, 1H), 1.44–1.54 ppm (2t, 3H). |
| 1.006 | —CH₃ | —CH(CH₃)—C₆H₅ | ¹H-NMR (200 MHz, CDCl₃): 7.20–7.75 ppm (m, 8H), 6.38 ppm (s, 1H), 6.06 ppm (q, 1H), 5.63 ppm (m, 1H), 3.54 ppm (s, 3H), 2.52–3.02 ppm (m and q, 5H), 1.42–1.68 ppm (d, 3H). |
| 1.007 | —CH₃ | —CH(CH₃)₂ | m.p. 159–161° C. |
| 1.008 | —(CH₂)₅— | | ¹H-NMR (200 MHz, CDCl₃): 7.73 ppm (d, 1H), 7.59 ppm (d, 1H), 7.28 ppm (dxd, 1H), 6.38 ppm (m, 1H), 5.52 ppm (m, 1H), 3.38–3.62 ppm (m and s, 7H), 2.72 ppm (m, 2H), 1.44–1.72 ppm (d and m, 9H). |
| 1.009 | —C₂H₅ | —C₂H₅ | ¹H-NMR (200 MHz, CDCl₃): 7.70 ppm (d, 1H), 7.57 ppm (d, 1H), 7.28 ppm (dxd, 1H), 6,37 ppm (s, 1H), 5,58 ppm (m, 1H), 3.56 ppm (s, 3H), 3.20–3.52 ppm (m, 4H), 2.70 ppm (m, 2H), 1.04–1.24 ppm (2t, 6H). |
| 1.010 | —CH₃ | —C₂H₅ | ¹H-NMR (200 MHz, CDCl₃): 7.70 ppm (d, 1H), 7.57 ppm (d, 1H), 7.28 ppm (dxd, 1H), 6.38 ppm (s, 1H), 5.56 ppm (m, 1H), 3.58 ppm (s, 3H), 3.32–3.54 ppm (m, 2H), 2.44–3.02 ppm (m and 2s, 5H), 1.48 ppm (d, 3H), 1.03–1.26 ppm (2t, 3H). |
| 1.011 | —H | —CH₃ | m.p. 162–163° C. |
| 1.012 | —CH₃ | —CH₃ | ¹H-NMR (200 MHz, CDCl₃): 7.70 ppm (d, 1H), 7.57 ppm (d, 1H), 7.28 ppm (dxd, 1H), 6.38 ppm (m, 1H), 3.58 ppm (s, 3H), 2.44–2.96 ppm (m and 2s, 8H), 1.47 ppm (d, 3H). |
| 1.013 | —H | —CH(CH₃)₂ | m.p. 161–163° C. |

Example P2

Carboxyl-1-methylethyl-2-chloro-5-[3,6-dihydro-3-methyl-2,6-dioxo-4-trifluoromethyl-1(2H)-pyrimidinyl]benzoate (compound 2.001)

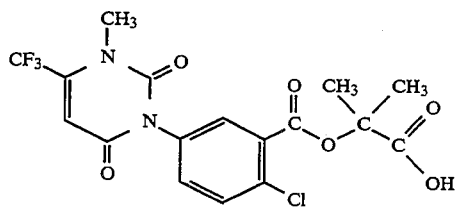
(2.001)

A mixture of 82.0 g of 2-chloro-5-[3,6-dioxo-3-methyl-4-trifluoromethyl-1(2H)-pyrimidinyl]benzoic acid and 83.3 g of thionyl chloride in 700 ml of toluene is heated for 2 hours to reflux temperature. The mixture is evaporated to dryness and the residue is dissolved in 600 ml of 1,2-dimethoxyethane. After the dropwise addition of this solution at a temperature of 10°–15° C. to a solution of 28.3 g of triethylamine, 0.5 g of 4-dimethylaminopyridine and 29.15 g of α-hydroxyisobutyric acid in 200 ml of 1,2-dimethoxyethane, the reaction mixture is stirred for 1 hour at 55° C. After extraction with 1000 ml of water and with 3×350 ml of ethyl acetate, the organic phase is washed once with 350 ml of water and concentrated by evaporation. The residue is recrystallised from ethyl acetate/n-hexane. The desired product, carboxyl-1-methylethyl-2-chloro-5-[3,6-dihydro-3-methyl-2,6-dioxo-4-trifluoromethyl-1(2H)-pyrimidinyl]benzoate has a melting point of 202°–203.5° C. $^1$H-NMR (D$_6$-DMSO, 200 MHz): 13.1 ppm (s,1H), 7.79 ppm (d,1H), 7.74 ppm (d,1H), 7.53 ppm (dxd,1H), 6.56 ppm (s,1H), 3.40 ppm (s,3H), 1.60 ppm (s,6H).

Example P3

1-(Allylcarbamoyl)-1-methylethyl-2-chloro-5-[3,6-dihydro-3-methyl-2,6-dioxo-4-trifluoromethyl-1(2H)-pyrimidinyl]benzoate (compound 2.002)

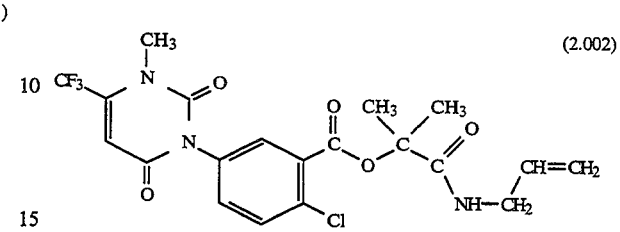
(2.002)

A mixture of 5.57 g of carboxyl-1-methylethyl-2-chloro-5-[3,6-dihydro-3-methyl-2,6-dioxo-4-trifluoromethyl-1(2H)-pyrimidinyl]benzoate, 4.57 g thionyl chloride and 0.1 ml of dimethyl formamide in 40 ml of toluene is stirred for 4 hours at 70° C. The reaction mixture is concentrated to dryness and the residue is dissolved in 40 ml of 1,2-dimethoxyethane. This solution is added dropwise at 15°–20° C. to a mixture of 1.41 g of triethylamine, 0.73 g of allylamine and 0.01 g of 4-dimethylaminopyridine in 40 ml of 1,2-dimethoxyethane and the mixture is stirred for 2 hours. The reaction mixture is poured into 200 ml of water which has been acidified with 4 ml of 2N hydrochloric acid. After extraction with 3×50 ml of ethyl acetate, the combined organic phases are washed with 2×50 ml of water until neutral and dried and, after dilution with 150 ml of n-hexane, filtered over silica gel. The eluate is concentrated by evaporation and the residue is recrystallised from ethyl acetate/n-hexane. The desired product, 1-(allylcarbamoyl)-1-methylethyl-2-chloro-5-[3,6-dihydro-3-methyl-2,6-dioxo-4-trifluoromethyl-1(2H)-pyrimidinyl]benzoate, has a melting point of 122°–124° C. $^1$H-NMR, (CDCl$_3$ 200 MHz): 13.1 ppm (s,1H), 7.70 ppm (d,1H), 7.60 ppm (d,1H), 7.42 ppm (dxd,1H), 6.38 ppm (s,1H), 5.76–5.96 ppm (m,1H), 5.10–5.29 ppm (m,2H), 3.92 ppm (m,2H), 3.55 ppm (s,3H), 1.80 ppm (s,6H).

The compounds of formula Ii listed in Table 2 are prepared in general accordance with the preparation of compound 2.002.

TABLE 2

Compounds of formula Ii:

| Cmpd. | R$_{10}$ | R$_{11}$ | Physico-chemical data |
|---|---|---|---|
| 2.003 | | —(CH$_2$)$_4$— | m.p. 169–170° C. |
| 2.004 | —CH$_3$ | phenyl | m.p. 190–192° C. |

TABLE 2-continued

Compounds of formula Ii:

(Ii)

| Cmpd. | $R_{10}$ | $R_{11}$ | Physico-chemical data |
|---|---|---|---|
| 2.005 | —H | phenyl | m.p. 119–120° C. |
| 2.006 | n-C$_3$H$_7$ | n-C$_3$H$_7$ | m.p. 151–152° C. |
| 2.007 | —H | cyclopropyl | m.p. 174–175° C. |
| 2.008 | —CH$_3$ | —C$_2$H$_5$ | m.p. 179–180° C. |
| 2.009 | —C$_2$H$_5$ | —C$_2$H$_5$ | m.p. 154–157° C. |
| 2.010 | —CH$_3$ | —CH$_3$ | m.p. 200–202° C. |
| 2.011 | —H | —CH$_3$ | m.p. 227–228° C. |
| 2.012 | —H | —C$_2$H$_5$ | m.p. 202–204° C. |
| 2.013 | —H | —CH$_2$—C≡CH | m.p. 157–157,5° C. |
| 2.014 | —(CH$_2$)$_5$— | | m.p. 122–125° C. |
| 2.015 | —H | n-C$_3$H$_7$ | $^1$H-NMR (CDCl$_3$, 200 MHz): 7.70 ppm (d, 1H), 7.60 ppm (d, 1H), 7.32 ppm (dxd, 1H), 6.48 ppm (t, 1H), 6.39 ppm (s, 1H), 3.56 ppm (s, 3H), 3.26 ppm (m, 2H), 1.80 ppm (s, 6H), 1.55 ppm (q, 2H), 0.92 ppm (t, 3H). |
| 2.016 | —H | —CH(CH$_3$)$_2$ | m.p. 127–128° C. |
| 2.017 | —H | —CH(CH$_3$)—C(O)OC$_2$H$_5$ (S) | $^1$H-NMR (CDCl$_3$, 200 MHz): 7.78 ppm (d, 1H), 7.61 ppm (d, 1H), 7.32 ppm (dxd, 1H), 6.98 ppm (d, 1H), 6.38 ppm (s, 1H), 4.58 ppm (q, 1H), 4.19 ppm (q, 2H), 3.56 ppm (s, 3H), 1.80 ppm (s, 6H), 1.43 ppm (d, 3H), 1.27 ppm (t, 1H). |
| 2.018 | —H | —CH$_2$—C(O)OC$_2$H$_5$ | $^1$H-NMR (CDCl$_3$, 200 MHz): 7.79 ppm (d, 1H), 7.61 ppm (d, 1H), 7.32 ppm (dxd, 1H), 6.92 ppm (t, 1H), 6.38 ppm (s, 1H), 4.47 ppm (d, 2H), 4.20 ppm (q, 2H), 3.56 ppm (s, 3H), 1.82 ppm (s, 6H), 1.27 ppm (t, 3H). |
| 2.019 | —CH$_3$ | —CH$_2$—C(O)OC$_2$H$_5$ | m.p. 182–184° C. |
| 2.020 | —H | —C(CH$_3$)$_2$—C≡CH | m.p. 105–108° C. |
| 2.021 | —H | —H | m.p. 230° C. |
| 2.022 | —H | —CH$_2$CN | m.p. 209–210° C. |
| 2.023 | —H | —CH$_2$CH$_2$OCH$_3$ | m.p. 115–116° C. |

TABLE 2-continued

Compounds of formula Ii:

(Ii)

[structure diagram]

| Cmpd. | R10 | R11 | Physico-chemical data |
|---|---|---|---|
| 2.024 | —CH3 | —OCH3 | m.p. 128–129° C. |
| 2.025 | —H | —OC2H5 | |
| 2.026 | —H | —O—CH2—C(CH2)=CH | |

Example P4

1-(Allylcarbamoyl)methyl-2-chloro-5-[3,6-dihydro-3-methyl-2,6-dioxo-4-trifluoromethyl-1(2H)-pyrimidinyl]benzoate (compound 3.001)

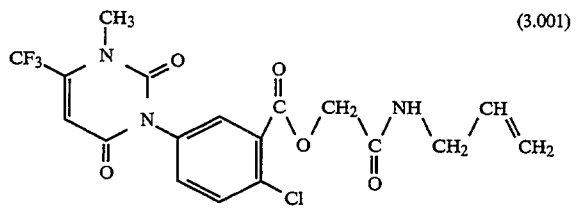

(3.001)

0.34 g of a 60% dispersion of sodium hydride in oil is charged to 50 ml of dimethyl formamide. Then 3.0 g of 2-chloro-5-[3,6-dihydro-3-methyl-2,6-dioxo-4-tri-fluoromethyl-1(2H)-pyrimidinyl]benzoic acid are added. After the evolution of hydrogen has ceased, 1.69 g of 2-bromoacetallylamide is added and the reaction mixture is stirred for 2 hours at room temperature. The reaction solution is poured into 300 ml of water and extracted with 2×75 ml of ethyl acetate. The combined organic phases are washed with 100 ml of a 5% solution of sodium hydrogencarbonate and 100 ml of water and concentrated. The crude product is recrystallised from ethyl acetate/diethyl ether. The 1-(allylcarbamoyl)-methyl-2-chloro-5-[3,6-dihydro-3-methyl-2,6-dioxo-4-trifluoromethyl-1(2H)-pyrimidinyl]benzoate melts at 187°–188° C.

1-(Allylcarbamoyl)-1-ethyl-2-chloro-5-[3,6-dihydro-3-methyl-2,6-dioxo-4-trifluoromethyl-1(2H)-pyrimidinyl]benzoate which melts at 178°–180° C. is prepared in general accordance with the process for obtaining compound 3.001 (compound 3.002)

The compounds of formulae Ie and If listed in Tables 3 and 4 are prepared in general accordance with Examples P1 P4.

TABLE 3

Compounds of formula Ie

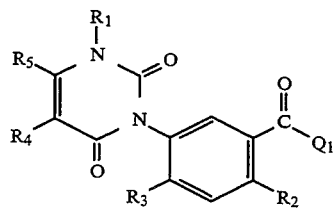

(Ie)

| Cmpd. | R1 | R2 | R3 | R4 | R5 | Q1 | Physico-chemical data |
|---|---|---|---|---|---|---|---|
| 3.003 | —CH3 | —Cl | —F | —H | —CF3 | —O—C(CH3)2—CONHCH3 | |
| 3.004 | —CH3 | —Cl | —H | —H | —CF3 | —O—C(CH3)2—CONHCH3 | |
| 3.005 | —CH3 | —Cl | —F | —H | —CF3 | —O—C(CH3)2—CONHC2H5 | |
| 3.006 | —CH3 | —Cl | —F | —H | —CF3 | —O—C(CH3)2—CONHC3H7 | |
| 3.007 | —CH3 | —Cl | —H | —H | —CF3 | —O—C(CH3)2—CON(C2H5)2 | |

TABLE 3-continued
Compounds of formula Ie (Ie)

| Cmpd. | $R_1$ | $R_2$ | $R_3$ | $R_4$ | $R_5$ | $Q_1$ | Physico-chemical data |
|---|---|---|---|---|---|---|---|
| 3.008 | $-CH_3$ | $-Cl$ | $-F$ | $-H$ | $-CF_3$ | $-O-C(CH_3)_2-CONHCH_2CH=CH_2$ | |
| 3.009 | $-CH_3$ | $-Cl$ | $-H$ | $-H$ | $-CF_3$ | $-O-C(CH_3)_2-CONHCH_2CH=CH_2$ | |
| 3.010 | $-CH_3$ | $-Cl$ | $-F$ | $-H$ | $-CF_3$ | $-O-C(CH_3)_2-CONHCH_2C\equiv CH$ | |
| 3.011 | $-CH_3$ | $-Cl$ | $-F$ | $-H$ | $-CF_3$ | $-O-C(CH_3)_2-CONHCH(CH_3)C\equiv CH$ | |
| 3.012 | $-CH_3$ | $-Cl$ | $-F$ | $-H$ | $-CF_3$ | $-O-C(CH_3)_2-CONHC(CH_3)_2C\equiv CH$ | |
| 3.013 | $-CH_3$ | $-Cl$ | $-F$ | $-H$ | $-CF_3$ | $-O-C(CH_3)_2-CONHCH(CH_3)CH=CH_2$ | |
| 3.014 | $-CH_3$ | $-Cl$ | $-F$ | $-H$ | $-CF_3$ | $-O-C(CH_3)_2-CONH-\text{cyclopropyl}$ | |
| 3.015 | $-CH_3$ | $-Cl$ | $-H$ | $-H$ | $-CF_3$ | $-O-C(CH_3)_2-CONH-\text{cyclopropyl}$ | |
| 3.016 | $-CH_3$ | $-Cl$ | $-F$ | $-H$ | $-CF_3$ | $-O-C(CH_3)_2-CONHCH_2COOCH_3$ | |
| 3.017 | $-CH_3$ | $-Cl$ | $-F$ | $-H$ | $-CF_3$ | $-O-C(CH_3)_2-CONHCH(CH_3)COOCH_3$ | |
| 3.018 | $-CH_3$ | $-Cl$ | $-F$ | $-H$ | $-CF_3$ | $-O-C(CH_3)_2-CON(CH_3)_2$ | |
| 3.019 | $-CH_3$ | $-Cl$ | $-F$ | $-H$ | $-CF_3$ | $-O-C(CH_3)_2-CON(C_2H_5)_2$ | |
| 3.020 | $-CH_3$ | $-Cl$ | $-F$ | $-H$ | $-CF_3$ | $-O-C(CH_3)_2-CON(C_3H_7)_2$ | |
| 3.021 | $-CH_3$ | $-Cl$ | $-H$ | $-H$ | $-CF_3$ | $-O-C(CH_3)_2-CON(C_3H_7)_2$ | |
| 3.022 | $-CH_3$ | $-Cl$ | $-F$ | $-H$ | $-CF_3$ | $-O-CH(S)-CH_2-CONHCH_3$ | |
| 3.023 | $-CH_3$ | $-Cl$ | $-F$ | $-H$ | $-CF_3$ | $-O-CH(S)-CH_2-CON(CH_3)_2$ | |

TABLE 3-continued

Compounds of formula Ie (Ie)

[Structure: pyrimidine-2,4-dione with R1 on N, R5 and R4 on ring carbons, N-linked to phenyl ring bearing R3, R2, and C(=O)Q1]

| Cmpd. | R₁ | R₂ | R₃ | R₄ | R₅ | Q₁ | Physico-chemical data |
|---|---|---|---|---|---|---|---|
| 3.024 | —CH₃ | —Cl | —F | —H | —CF₃ | —O—(S)CH—CH₂—CONHC₂H₅ | |
| 3.025 | —CH₃ | —Cl | —F | —H | —CF₃ | —O—(S)CH—CH₂—CONHCH₂CH=CH₂ | |
| 3.026 | —CH₃ | —Cl | —F | —H | —CF₃ | —O—(S)CH—CH₂—CONHCH₂C≡CH | |
| 3.027 | —CH₃ | —Cl | —F | —H | —CF₃ | —O—C(CH₃)₂—CONHCH₃ | |
| 3.028 | —CH₃ | —Cl | —H | —H | —CF₃ | —O—C(CH₃)₂—CONHCH₃ | |
| 3.029 | —CH₃ | —Cl | —F | —H | —CF₃ | —O—C(CH₃)₂—CONHC₂H₅ | |
| 3.030 | —CH₃ | —Cl | —F | —H | —CF₃ | —O—C(CH₃)₂—CONHC₃H₇ | |
| 3.031 | —CH₃ | —Cl | —F | —H | —CF₃ | —O—C(CH₃)₂—CON(CH₃)₂ | |
| 3.032 | —CH₃ | —Cl | —F | —H | —CF₃ | —O—C(CH₃)₂—CONHCH₂CH=CH₂ | |
| 3.033 | —CH₃ | —Cl | —F | —H | —CF₃ | —O—CH(CH₃)—CONHCH₃ | |
| 3.034 | —CH₃ | —Cl | —F | —CH₃ | —CF₃ | —O—C(CH₃)₂—CONHC₂H₅ | |
| 3.035 | —CH₃ | —Cl | —F | —Cl | —CF₃ | —O—C(CH₃)₂—CONHCH₃ | |
| 3.036 | —CH₃ | —Cl | —F | —F | —CF₃ | —O—C(CH₃)₂—CONHC₂H₅ | |
| 3.037 | —CH₃ | —Cl | —F | —Br | —CF₃ | —O—C(CH₃)₂—CONHC₃H₇ | |
| 3.038 | —CH₃ | —Cl | —F | —H | —CF₃ | —O—C(CH₃)₂—CONHCH₃ | |
| 3.039 | —CH₃ | —Cl | —F | —H | —CF₃ | —O—C(CH₃)₂—CONHC₂H₅ | |

TABLE 3-continued
Compounds of formula Ie (Ie)

| Cmpd. | R₁ | R₂ | R₃ | R₄ | R₅ | Q₁ | Physico-chemical data |
|---|---|---|---|---|---|---|---|
| 3.040 | —CH₃ | —Cl | —F | —H | —CF₃ | —O—(cyclopropyl)—CONHC₂H₅ | |
| 3.041 | —CH₃ | —Cl | —F | —H | —C₂F₅ | —O—C(CH₃)₂—CONHC₂H₅ | |
| 3.042 | —CH₃ | —Cl | —F | —H | —C₂F₅ | —O—C(CH₃)₂—CONHCH₃ | |
| 3.043 | —CH₃ | —Cl | —F | —H | —C₂F₅ | —O—C(CH₃)₂—CONHC₃H₇ | |
| 3.044 | —CH₃ | —Cl | —F | —H | —C₂F₅ | —O—C(CH₃)₂—CONHCH₂CH=CH₂ | |
| 3.045 | —CH₃ | —Cl | —F | —H | —C₂F₅ | —O—C(CH₃)₂—CONHCH₂C≡CH | |
| 3.046 | —CH₃ | —Cl | —F | —H | —C₂F₅ | —O—C(CH₃)₂—CONHCH(CH₃)C≡CH | |
| 3.047 | —CH₃ | —Cl | —F | —H | —C₂F₅ | —O—C(CH₃)₂—CONHC(CH₃)₂C≡CH | |
| 3.048 | —CH₃ | —Br | —F | —H | —CF₃ | —O—C(CH₃)₂—CONHCH₃ | |
| 3.049 | —CH₃ | —CN | —F | —H | —CF₃ | —O—C(CH₃)₂—CONHC₂H₅ | |
| 3.050 | —CH₃ | —Br | —H | —H | —CF₃ | —O—C(CH₃)₂—CONHC₃H₇ | |
| 3.051 | —CH₃ | —CN | —H | —H | —CF₃ | —O—C(CH₃)₂—CONHCH₂CH=CH₂ | |
| 3.052 | —CH₃ | —Br | —F | —H | —C₂F₅ | —O—C(CH₃)₂—CONHCH₂C≡CH | |
| 3.053 | —CH₃ | —CN | —F | —H | —C₂F₅ | —O—C(CH₃)₂—CONHCH(CH₃)C≡CH | |
| 3.054 | —CH₃ | —CN | —F | —CH₃ | —CF₃ | —O—C(CH₃)₂—CONHC₂H₅ | |
| 3.055 | —CH₃ | —Br | —F | —C₂H₅ | —CF₃ | —O—C(CH₃)₂—CONHC₂H₅ | |

TABLE 3-continued
Compounds of formula Ie

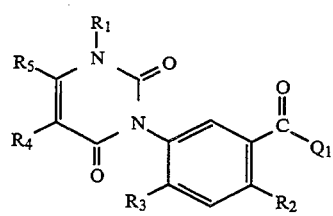

(Ie)

| Cmpd. | $R_1$ | $R_2$ | $R_3$ | $R_4$ | $R_5$ | $Q_1$ | Physico-chemical data |
|---|---|---|---|---|---|---|---|
| 3.056 | —$CH_3$ | —Cl | —F | —$CH_3$ | —$CH_3$ | —O—C($CH_3$)$_2$—CONHC$_2$H$_5$ | |
| 3.057 | —$CH_3$ | —Cl | —F | —H | —$CH_3$ | —O—C($CH_3$)$_2$—CONHC$_2$H$_5$ | |
| 3.058 | —$CH_3$ | —Cl | —F | —H | —$C_2H_5$ | —O—C($CH_3$)$_2$—CONHC$_3$H$_7$ | |
| 3.059 | —$CHF_2$ | —Cl | —F | —H | —$CH_3$ | —O—C($CH_3$)$_2$—CONHC$_2$H$_5$ | |
| 3.060 | —$CHF_2$ | —Cl | —F | —H | —$CH_3$ | —O—C($CH_3$)$_2$—CONHCH$_3$ | |
| 3.061 | —$CF_3$ | —Cl | —F | —H | —$CH_3$ | —O—C($CH_3$)$_2$—CONHCH$_3$ | |
| 3.062 | —$CH_3$ | —Cl | —F | —H | —$CF_3$ | —O—C($CH_3$)$_2$—CO—N(pyrrolidine) | |
| 3.063 | —$CH_3$ | —Cl | —H | —H | —$CF_3$ | —O—C($CH_3$)$_2$—CO—N(pyrrolidine) | |

TABLE 4
Compounds of formula If

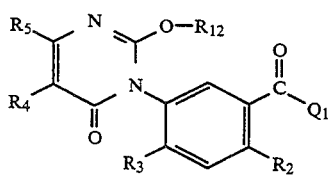

(If)

| Cmpd. | $R_{12}$ | $R_2$ | $R_3$ | $R_4$ | $R_5$ | $Q_1$ | Physico-chemical data |
|---|---|---|---|---|---|---|---|
| 4.001 | —$CH_3$ | —Cl | —F | —H | —$CF_3$ | —O—C($CH_3$)$_2$—CONHCH$_3$ | |
| 4.002 | —$CH_3$ | —Cl | —F | —H | —$C_2F_5$ | —O—C($CH_3$)$_2$—CONHC$_2$H$_5$ | |
| 4.003 | —$CH_3$ | —Cl | —F | —F | —$CF_3$ | —O—C($CH_3$)$_2$—CONHC$_3$H$_7$ | |

TABLE 4-continued

Compounds of formula If

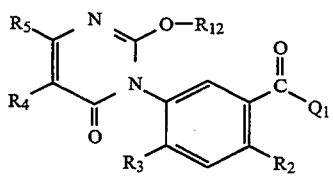

| Cmpd. | R₁₂ | R₂ | R₃ | R₄ | R₅ | Q₁ | Physico-chemical data |
|---|---|---|---|---|---|---|---|
| 4.004 | —CH₃ | —Cl | —F | —Cl | —C₂F₅ | —O—C(CH₃)₂—CONHCH₂CH=CH₂ | |
| 4.005 | —CH₃ | —CN | —F | —H | —CF₃ | —O—C(CH₃)₂—CONHCH₃ | |
| 4.006 | —CH₃ | —CN | —H | —H | —CF₃ | —O—C(CH₃)₂—CONHC₂H₅ | |
| 4.007 | —CH₃ | —CN | —F | —H | —CH₃ | —O—C(CH₃)₂—CONHC₂H₅ | |
| 4.008 | —CH₃ | —Cl | —F | —H | —CH₃ | —O—C(CH₃)₂—CONHC₂H₅ | |
| 4.009 | —CH₃ | —Cl | —F | —CH₃ | —CH₃ | —O—C(CH₃)₂—CONHC₂H₅ | |
| 4.010 | —CH₃ | —Cl | —F | —CH₃ | —CF₃ | —O—C(CH₃)₂—CONHC₃H₇ | |
| 4.011 | —CH₃ | —Br | —F | —H | —CF₃ | —O—C(CH₃)₂—CONHC₂H₅ | |
| 4.012 | —CH₃ | —Br | —H | —H | —CF₃ | —O—C(CH₃)₂—CON(CH₃)₂ | |
| 4.013 | —CH₃ | —Cl | —F | —H | —CF₃ | —O—CH(S)(CH₃)—CONHCH₃ | |
| 4.014 | —CH₃ | —Cl | —F | —H | —CF₃ | —O—CH(S)(CH₃)—CON(CH₃)₂ | |
| 4.015 | —CH₃ | —Cl | —H | —H | —CF₃ | —O—CH(S)(CH₃)—CONHC₂H₅ | |
| 4.016 | —CH₃ | —Cl | —H | —H | —CF₃ | —O—C(CH₃)₂—CONHCH₃. | |

B. FORMULATION EXAMPLES

Example F1

The following constituents are mixed with one another to prepare a 25% wettable powder:

| | % by weight |
|---|---|
| compound of formula I (herbicide) | 25 |
| hydrated silica (carrier, grinding assistant) | 20 |
| sodium laurylsulfate (wetting agent) | 2 |
| sodium liposulfonate (dispersant) | 4 |
| kaolin (carrier) | 49 |
| | 100 |

The liquid or fused herbicide is first applied to the silica in a milling apparatus. The further constituents are then added. The mixture is finely milled using a pin mill or another comparable milling apparatus.

When stirred into water, the resultant wettable powder forms a fine suspension of any concentration which is suitable for use as a ready-for-use spray mixture.

Particularly suitable herbicides for this formulation are compounds of formula I which are liquid or have a low melting point, i.e. up to c. +100° C.

Example F2

Compounds of formula I with a high melting point, i.e. from c. +100° C., can preferably be used as herbicides in concentrated wettable powders, typically as follows:

| | % by weight |
|---|---|
| compound of formula I (herbicide) | 75 |
| hydrated silica (carrier, grinding assistant) | 1 |
| alkylnaphthalenesulfonate and alkylcarboxylate sulfate as sodium salts, typically "Morowett EFW" (reg. trademark of De Soto) (wetting agent) | 2 |
| sulfonated naphthalene-formaldehyde condensate as sodium salt, typically "Morowett D-425" (reg. trademark of De Soto) (dispersant) | 10 |
| polyvinylpyrrolidone, e.g. PVP-K-30 (GAF Corp.) (binder) | 1 |
| kaolin (carrier) | 11 |
| | 100 |

The constituents are mixed with one another using a pin mill or another comparable milling apparatus, preferably a jet mill.

When stirred into water, the resultant wettable powder forms a fine suspension of any concentration which is suitable for use as a ready-for-use spray mixture.

Example F3

A wettable powder based on the formulation of compound 2.002 can also be convened into a dispersible granulate. This is done by spraying the milled powder in a suitable granulator (e.g. a granulating pan, mixer drum, impeller or fluidised bed granulator) with an aqueous solution of the binder until agglomerates form. Afterwards the water added is removed in a drying step. The granules of the desired size are sieved out.

The granular formulation so obtained has advantages over the wettable powder (no dust formation when applied, easier addition owing to enhanced flow properties). Application is made by stirring the formulation into water and, after complete disintegration of the granules to the primary particles, the procedure is exactly the same as for the wettable powders.

Example F4

The compounds of formula I have limited solubility in customary organic solvents. Accordingly, it is possible to prepare emulsifiable concentrates of relatively low concentration, as e.g.:

| | |
|---|---|
| compound of formula I (herbicide) | 125 g/l |
| "Sorprophor BSU" (reg. trademark of Rhône-Poulenc) (emulsifier) | 300 g/l |
| N-methyl-2-pyrrolidone (solvent) to make up | 1000 ml |

With stirring, the herbicide and the emulsifier are added to the solvent. The mixture is stirred until a homogeneous solution is obtained.

The resultant emulsifiable concentrate can be emulsified in water and forms a ready-for-use spray mixture of the desired concentration.

Example F5

Compounds of formula I with a melting point from c. +60° C. can also be formulated as suspension concentrates (flowables);

| | |
|---|---|
| compound of formula I (herbicide) | 250 g/l |
| ethylene glycol (antifreeze agent) | 80 g/l |
| silica (antiprecipitant) | 5 g/l |
| xanthan gum, e.g. "Kelzan" (reg. trademark of Kelco) (thickener) | 2 g/l |
| silicon antifoam, e.g. "Rhodorsil 426" (reg. trademark of Rhône-Poulenc) | 5 g/l |
| nonylphenol polyethoxylate (wetting agent) | 20 g/l |
| sulfonated naphthalene-formaldehyde condensate as sodium salt, e.g. "Morowett D-425" (reg. trademark of De Soto) (dispersant) | 40 g/l |
| water to make up | 1000 ml |

The formulation assistants are dissolved in water. The pre-milled herbicide is dispersed, with stirring, in the solution. The resultant coarse suspension is then subjected to wet milling (conveniently in a colloid mill or a stirred ball mill). Minor amounts of further optional ingredients such as antifoams, antiprecipitants and biocides may then be added.

For application, the resultant flowable can be diluted in all proportions with water to give a ready-for-use spray mixture of the desired concentration.

C. BIOLOGICAL EXAMPLES

Example B1

Pre-Emergence Herbicidal Action

Monocot and dicot test plants are sown in plastic pots in standard soil. Immediately after sowing, an aqueous suspension of the test compound prepared from a 25% wettable powder (Example F1) is sprayed on to the plants in concentrations of 4 kg and 2 kg a.i./ha (500 l of water/ha). The test plants are then cultivated in a greenhouse under optimum conditions. The test is evaluated after 3 weeks on a rating scale from 1 to 9(1=total damage, 9=no action). Ratings from 1 to 4 (especially from 1 to 3) denote good to very good herbicidal action. The same result is obtained with a wettable powder concentrate (Example F2), dispersible granulate (Example F3), emulsifiable concentrate (Example F4) and suspension concentrate (flowable) (Example F5).

Test plants: Avena, Setaria, Sinapis, Stellaria.

In this test the compounds of formula I according to the Examples in Tables 1 to 4 exhibit strong herbicidal action.

Examples of the good herbicidal action of the compounds of formula I are shown in Table B1:

TABLE B1

| | | Preemergence action | | | |
|---|---|---|---|---|---|
| Cmpd. | Conc. [kg ai/ha] | Avena | Setaria | Sinapis | Stellaria |
| 1.001 | 4 | 1 | 1 | 1 | 1 |
| 1.002 | 4 | 1 | 1 | 1 | 1 |
| 1.003 | 4 | 1 | 1 | 1 | 1 |
| 1.004 | 4 | 1 | 1 | 1 | 1 |
| 1.005 | 4 | 1 | 1 | 1 | 1 |

TABLE B1-continued

| | | Preemergence action | | | |
|---|---|---|---|---|---|
| Cmpd. | Conc. [kg ai/ha] | Avena | Setaria | Sinapis | Stellaria |
| 1.006 | 4 | 1 | 1 | 1 | 1 |
| 1.007 | 4 | 1 | 1 | 1 | 1 |
| 1.008 | 4 | 1 | 1 | 1 | 1 |
| 1.009 | 4 | 1 | 1 | 1 | 1 |
| 1.010 | 4 | 1 | 1 | 1 | 1 |
| 1.011 | 4 | 1 | 1 | 1 | 1 |
| 1.013 | 4 | 1 | 1 | 1 | 1 |
| 2.002 | 4 | 1 | 1 | 1 | 1 |
| 2.003 | 2 | 1 | 1 | 1 | 1 |
| 2.004 | 2 | 1 | 1 | 1 | 1 |
| 2.005 | 2 | 1 | 1 | 1 | 1 |
| 2.006 | 2 | 1 | 1 | 1 | 1 |
| 2.007 | 2 | 1 | 1 | 1 | 1 |
| 2.008 | 2 | 1 | 1 | 1 | 1 |
| 2.009 | 4 | 1 | 1 | 1 | 1 |
| 2.010 | 2 | 1 | 1 | 1 | 1 |
| 2.011 | 2 | 1 | 1 | 1 | 1 |
| 2.012 | 2 | 1 | 1 | 1 | 1 |
| 2.013 | 2 | 1 | 1 | 1 | 1 |
| 2.014 | 2 | 1 | 1 | 1 | 1 |
| 2.015 | 2 | 1 | 1 | 1 | 1 |
| 2.016 | 4 | 1 | 1 | 1 | 1 |
| 2.017 | 2 | 1 | 1 | 1 | 1 |
| 2.018 | 2 | 2 | 1 | 1 | 1 |
| 2.019 | 2 | 1 | 1 | 1 | 1 |
| 2.020 | 2 | 1 | 1 | 1 | 1 |
| 2.021 | 2 | 1 | 1 | 1 | 1 |

Example 2

Post-Emergence Herbicidal Action (Contact Herbicide)

Monocot and dicot plants are cultivated in a greenhouse in plastic pots with standard soil and sprayed in the 4- to 6-leaf stage with an aqueous suspension prepared from a 25% wettable powder (Example F1) of the test compound in a concentration of 4 kg and 2 kg a.i./ha (500 l of water/ha). The test plants are then cultivated in a greenhouse under optimum conditions. The test is evaluated after 3 weeks on a rating scale from 1 to 9 (1=total damage, 9=no action). Ratings from 1 to 4 (especially from 1 to 3) denote good to very good herbicidal action. The same result is obtained with a wettable powder concentrate (Example F2), dispersible granulate (Example F3), emulsifiable concentrate (Example F4) and suspension concentrate (flowable) (Example F5).

Test plants: Avena, Setaria, Sinapis, Stellaria.

In this test also the compounds of formula I according to the Examples in Tables 1 to 4 exhibit strong herbicidal action.

Examples of the good herbicidal action of the compounds of formula I are shown in Table B2:

TABLE B2

| | | Post-emergence action | | | |
|---|---|---|---|---|---|
| Cmpd. | Conc. [kg ai/ha] | Avena | Setaria | Sinapis | Stellaria |
| 1.001 | 4 | 1 | 1 | 1 | 1 |
| 1.002 | 4 | 1 | 1 | 1 | 1 |
| 1.003 | 4 | 1 | 1 | 1 | 1 |
| 1.004 | 4 | 1 | 1 | 1 | 1 |
| 1.005 | 4 | 1 | 1 | 1 | 1 |
| 1.006 | 4 | 1 | 1 | 1 | 1 |
| 1.007 | 4 | 1 | 1 | 1 | 1 |
| 1.008 | 4 | 1 | 1 | 1 | 1 |
| 1.009 | 4 | 1 | 1 | 1 | 1 |
| 1.010 | 4 | 1 | 1 | 1 | 1 |
| 1.011 | 4 | 1 | 1 | 1 | 1 |
| 1.013 | 4 | 1 | 1 | 1 | 1 |

TABLE B2-continued

| | | Post-emergence action | | | |
|---|---|---|---|---|---|
| Cmpd. | Conc. [kg ai/ha] | Avena | Setaria | Sinapis | Stellaria |
| 2.002 | 4 | 1 | 1 | 1 | 1 |
| 2.003 | 2 | 1 | 1 | 1 | 1 |
| 2.004 | 2 | 1 | 1 | 1 | 1 |
| 2.005 | 2 | 1 | 1 | 1 | 1 |
| 2.006 | 2 | 1 | 1 | 1 | 1 |
| 2.007 | 2 | 1 | 1 | 1 | 1 |
| 2.008 | 2 | 1 | 1 | 1 | 1 |
| 2.009 | 4 | 1 | 1 | 1 | 1 |
| 2.010 | 2 | 1 | 1 | 1 | 1 |
| 2.011 | 2 | 1 | 1 | 1 | 1 |
| 2.012 | 2 | 1 | 1 | 1 | 1 |
| 2.013 | 2 | 1 | 1 | 1 | 1 |
| 2.014 | 2 | 1 | 1 | 1 | 1 |
| 2.015 | 2 | 1 | 1 | 1 | 1 |
| 2.016 | 4 | 1 | 1 | 1 | 1 |
| 2.017 | 2 | 1 | 1 | 1 | 1 |
| 2.018 | 2 | 1 | 1 | 1 | 1 |
| 2.019 | 2 | 1 | 1 | 1 | 1 |
| 2.020 | 2 | 1 | 1 | 1 | 1 |
| 2.021 | 2 | 1 | 1 | 1 | 1 |

What is claimed is:

1. A 3-aryluracil compound of formula I

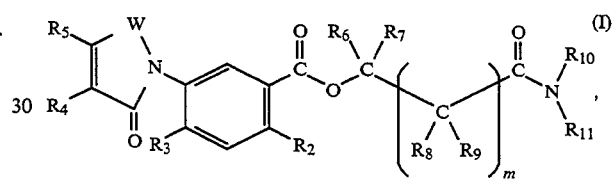

wherein

W is a group of formula

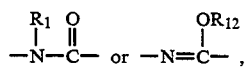

in which the linkage to the ring nitrogen atom is through the carbon atom:

$R_1$ is hydrogen, $C_1$-$C_4$alkyl, $C_1$-$C_4$haloalkyl, $C_3$- or $C_4$alkenyl or $C_3$- or $C_4$alkynyl;

$R_2$ is halogen or cyano;

$R_3$ is hydrogen or fluoro;

$R_4$ is hydrogen, halogen or $C_1$-$C_4$alkyl;

$R_5$ is $C_1$-$C_4$alkyl or $C_1$-$C_4$haloalkyl;

$R_6$ to $R_9$ are each independently of one another hydrogen, $C_1$-$C_4$alkyl, $C_3$-$C_6$alkenyl, $C_3$-$C_6$alkynyl $C_1$-$C_4$haloalkyl or phenyl; or $R_6$ and $R_7$ or $R_8$ and $R_9$, together with the linking carbon atom, form a 3-, 4-, 5- or 6-membered cycloalkane ring which may be substituted by one or more $C_1$-$C_4$alkyl groups; or $R_7$ and $R_9$, together with the linking carbon atoms, form a 3-, 4-, 5- or 6-membered cycloalkane ring which may be substituted by one or more $C_1$-$C_4$alkyl groups;

m is 0 or 1;

$R_{10}$ is hydrogen, $C_1$-$C_4$alkyl, $C_3$- or $C_4$alkenyl, $C_3$- or $C_4$alkynyl, $C_4$-$C_4$haloalkyl, $C_1$-$C_6$alkoxy-$C_1$-$C_4$alkyl, $C_1$-$C_6$alkylthio-$C_1$-$C_4$alkyl;

$R_{11}$ is hydrogen, $C_1$-$C_4$alkyl, $C_3$- or $C_4$alkenyl, $C_3$-$C_5$alkynyl, $C_1$-$C_4$haloalkyl, $C_1$-$C_6$alkoxy, $C_1$-$C_6$alkenyloxy, $C_1$-$C_6$alkoxy-$C_1$-$C_4$alkyl, $C_1$-$C_6$alkylthio-$C_1$-$C_4$alkyl, $C_3$-$C_6$cycloalkyl, $C_2$-$C_4$cyanoalkyl, $C_1$-$C_4$alkoxycarbonyl-$C_1$- or -$C_2$alkyl, carboxy-$C_1$- or -$C_2$alkyl, ($C_1$-$C_4$alkoxy)$_2$-P(O)-$C_1$- or -$C_2$alkyl, aryl, aryl-$C_1$-$C_4$alkyl, heteroaryl, heteroaryl-$C_1$-$C_4$alkyl, $C_3$-$C_6$cycloalkyl-$C_1$-$C_4$alkyl; or $R_{10}$ and $R_{11}$, together with the linking nitrogen atom, form a pyrrolidino, piperidino, hexahydroazepino, morpholino, 2,6-dimethylmorpholino, thiomorpholino, piperazino or 4-methylpiperazino ring; and $R_{12}$ is $C_1$-$C_4$alkyl, $C_3$- or $C_4$alkenyl or $C_3$- or $C_4$alkynyl; or when $R_1$ is hydrogen, an agrochemically acceptable salt of a compound of formula I.

2. A compound according to claim 1, wherein $R_2$ is chloro, bromo or cyano.

3. A compound according to claim 1, wherein $R_4$ is hydrogen, fluoro or methyl.

4. A compound according to claim 1, wherein $R_5$ is methyl, trifluoromethyl or pentafluoroethyl.

5. A compound according to claim 1, wherein $R_6$ to $R_9$ are each independently of one another hydrogen, methyl, ethyl, $C_3$- or $C_4$alkenyl, $C_3$- or $C_4$alkynyl, $C_1$- or $C_2$haloalkyl or phenyl; or $R_6$ and $R_7$ or $R_8$ and $R_9$, together with the linking carbon atom form a 3-, 4-, 5or 6-membered unsubstituted ring; or $R_7$ and $R_9$, together with the linking carbon atom, form a 3-, 4-, 5- or 6-membered unsubstituted ring.

6. A compound according to claim 1, wherein $R_{10}$ is hydrogen, $C_1$-$C_4$alkyl, allyl, methallyl, propargyl or methoxy- or ethoxy-$C_2$-$C_4$alkyl.

7. A compound according to claim 1, wherein $R_{11}$ is hydrogen, $C_1$-$C_4$alkyl, $C_3$- or $C_4$alkenyl, $C_3$-$C_5$alkynyl, $C_1$-$C_4$alkoxy, $C_1$-$C_4$alkenyloxy, methoxy- or ethoxy-$C_2$-$C_4$alkyl, cyclopropyl, methoxy- or ethoxycarbonyl-$C_1$- or -$C_2$alkyl, phenyl, benzyl, $C_6H_5CH(CH_3)$— or $C_3$-$C_6$cycloalkyl-$C_1$ alkyl or -$C_2$alkyl.

8. A compound according to claim 1, wherein $R_{10}$ and $R_{11}$, together with the linking nitrogen atom, form a pyrrolidino, piperidino, morpholino, 2,6-dimethylmorpholino or thiomorpholino ring.

9. A compound according to claim 1, wherein W and m are as defined; $R_2$ is chloro, bromo or cyano; $R_3$ is hydrogen or fluoro; $R_4$ is hydrogen, fluoro or methyl; $R_5$ is methyl, trifluoromethyl or pentafluoroethyl; $R_6$ to $R_9$ are each independently of one another hydrogen, methyl or ethyl; $R_{10}$ is hydrogen, $C_1$-$C_4$alkyl, allyl, methallyl or propargyl; $R_{11}$ is hydrogen, $C_1$-$C_4$alkyl, allyl, methallyl, $C_3$-$C_5$alkynyl, $C_1$- or $C_2$alkoxy, allyloxy, cyclopropyl, methoxy- or ethoxycarbonyl-$C_1$- or-$C_2$alkyl, phenyl, benzyl or $C_6H_5CH(CH_3)$—; or $R_{10}$ and $R_{11}$, together with the linking nitrogen atom, form a pyrrolidino, piperidino or morpholino ring.

10. A compound according to claim 9, wherein W is a radical of formula

$R_1$ is hydrogen, $C_1$-$C_4$alkyl, $C_1$-$C_4$haloalkyl, $C_3$- or $C_4$alkenyl or $C_3$- or $C_4$alkynyl; $R_2$is chloro, $R_3$and $R_4$ are hydrogen; $R_5$ is trifluoromethyl; $R_6$ and $R_7$ are each independently of the other hydrogen or methyl; m is 0 or 1; $R_8$ and $R_9$ are hydrogen of $C_1$-$C_4$alkyl; $R_{11}$ is hydrogen, $C_1$-$C_4$alkyl, allyl, $C_3$-$C_5$alkynyl, $C_1$- or $C_2$alkoxy, allyloxy, cyclopropyl, ethoxycarbonyl-$C_1$- or -$C_2$alkyl, phenyl, benzyl or $C_6H_5CH(CH_3)$—; or $R_{10}$ and $R_{11}$, together with the linking nitrogen atom, form a pyrrolidino, piperidino, or morpholino ring.

11. A compound according to claim 9, wherein W is a radical of formula

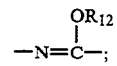

$R_{12}$ is $C_1$-$C_4$alkyl, $C_3$- or $C_4$alkenyl or $C_3$- or $C_4$alkynyl; $R_2$ is chloro, bromo or cyano; $R_3$ is hydrogen or fluoro; $R_4$ is hydrogen, fluoro, chloro or methyl; $R_5$ is methyl, trifluoromethyl or pentafluoroethyl; $R_6$ and $R_7$ are each independently of the other hydrogen or methyl; m is 0 or 1; $R_8$ and $R_9$ are hydrogen; $R_{10}$ is hydrogen or methyl; and $R_{11}$ is hydrogen, $C_1$-$C_4$alkyl or allyl.

12. A compound according to claim 9, wherein m is 1; $R_6$ is methyl; and $R_7$ is hydrogen.

13. A compound according to claim 1 of formula Ia,

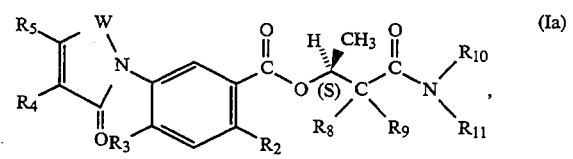

wherein W, $R_1$ to $R_5$ and $R_8$ to $R_{12}$ are as defined.

14. A compound according to claim 13 of formula Ib

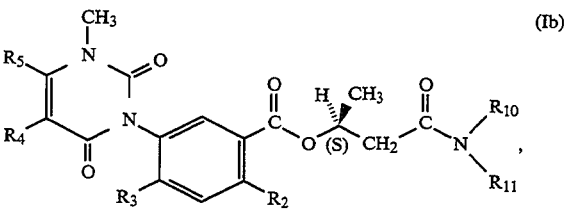

wherein $R_2$ is chloro, bromo or cyano; $R_3$ is hydrogen or fluoro; $R_4$ is hydrogen, methyl or fluoro; $R_5$ is methyl, trifluoromethyl or pentafluoroethyl; $R_{10}$ and $R_{11}$ are each independently of the other hydrogen or $C_1$-$C_4$alkyl.

15. A compound according to claim 10, wherein $R_1$ is hydrogen, methyl, allyl or propargyl.

16. A compound according to claim 15, wherein $R_1$ is methyl.

17. A compound according to claim 10 of formula Ic

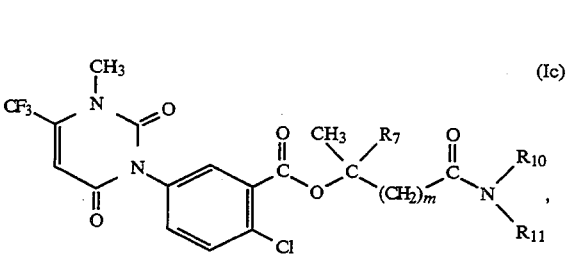

wherein $R_7$,m, $R_{10}$ and $R_{11}$ are as defined.

18. A compound according to claim 17 of formula Id (Id) [structure: CF3, CH3, N, O, Cl, C(CH3)2, NH-R11 substituted phenyl]

wherein $R_{11}$ is $C_1$-$C_4$alkyl, allyl, propargyl, $C_1$alkoxy or $C_2$alkoxy or allyloxy.

19. A herbicidal composition which comprises a herbicidally effective amount of a compound of formula I or a salt thereof as defined in claim 1 and a formulation assistant.

20. A composition according to claim 19, which contains from 0.1 to 95% by weight of the compound of formula I.

21. A method of controlling undesirable plant growth, which comprises treating the crop plants to be protected against weeds and the weeds with a herbicidally effective amount of a compound of formula I as defined in claim 1 or with a composition, which contains such a compound.

22. A method according to claim 21, wherein a compound of formula I is applied in a concentration of 0.001 to 2 Kg/ha.

23. A compound of formula VI (VI) [structure with W, R5, R4, OR3, R2, R6, R7, R8, R9, OH]

wherein
W is a group of formula $$-\underset{\underset{R_1}{|}}{N}-\underset{\underset{}{\overset{O}{\|}}}{C}- \text{ or } -N=\underset{\underset{}{|}}{\overset{OR_{12}}{C}}-,$$

in which the linkage to the ring nitrogen atom is through the carbon atom:

$R_1$ is hydrogen, $C_1$-$C_4$alkyl, $C_1$-$C_4$haloalkyl, $C_3$- or $C_4$alkenyl or $C_3$- or $C_4$alkynyl;
$R_2$ is halogen or cyano;
$R_3$ is hydrogen or fluoro;
$R_4$ is hydrogen, halogen or $C_1$-$C_4$alkyl;
$R_5$ is $C_1$-$C_4$alkyl or $C_1$-$C_4$haloalkyl;
$R_6$ to $R_9$ are each independently of one another hydrogen, $C_1$-$C_4$alkyl, $C_3$-$C_6$alkenyl, $C_3$-$C_6$alkynyl, $C_1$-$C_4$haloalkyl or phenyl; or
$R_6$ and $R_7$ or $R_8$ and $R_9$, together with the linking carbon atom, form a 3-, 4-, 5- or 6-membered cycloalkane ring which may be substituted by one or more $C_1$-$C_4$alkyl groups; or $R_7$ and $R_9$, together with the linking carbon atoms, form a 3-, 4-, 5- or 6-membered cycloalkane ring which may be substituted by one or more $C_1$-$C_4$alkyl groups; and
m is 0 or 1.

24. A compound of formula VIa (VIa) [structure with W, R5, R4, OR3, R2, R6, R7, R8, R9, Y]

wherein
W is a group of formula $$-\underset{\underset{R_1}{|}}{N}-\underset{\underset{}{\overset{O}{\|}}}{C}- \text{ or } -N=\underset{\underset{}{|}}{\overset{OR_{12}}{C}}-,$$

in which the linkage to the ring nitrogen atom is through the carbon atom:

$R_1$ is hydrogen, $C_1$-$C_4$alkyl, $C_1$-$C_4$haloalkyl, $C_3$- or $C_4$alkenyl or $C_3$- or $C_4$alkynyl;
$R_2$ is halogen or cyano;
$R_3$ is hydrogen or fluoro;
$R_4$ is hydrogen, halogen or $C_1$-$C_4$alkyl;
$R_5$ is $C_1$-$C_4$alkyl or $C_1$-$C_4$haloalkyl;
$R_6$ to $R_9$ are each independently of one another hydrogen, $C_1$-$C_4$alkyl, $C_3$-$C_6$alkenyl, $C_3$-$C_6$alkynyl, $C_1$-$C_4$haloalkyl or phenyl; or
$R_6$ and $R_7$ or $R_8$ and $R_9$, together with the linking carbon atom, form a 3-, 4-, 5- or 6-membered cycloalkane ring which may be substituted by one or more $C_1$-$C_4$alkyl groups; or $R_7$ and $R_9$, together with the linking carbon atoms, form a 3-, 4-, 5- or 6-membered cycloalkane ring which may be substituted by one or more $C_1$-$C_4$alkyl groups;
m is 0 or 1; and
Y is a leaving group.

* * * * *